(12) United States Patent
Shiina et al.

(10) Patent No.: US 8,382,670 B2
(45) Date of Patent: Feb. 26, 2013

(54) ULTRASONIC DIAGNOSIS SYSTEM AND DISTORTION DISTRIBUTION DISPLAY METHOD

(75) Inventors: Tsuyoshi Shiina, Ibaraki (JP); Makoto Yamakawa, Ibaraki (JP); Naotaka Nitta, Ibaraki (JP)

(73) Assignees: Tsuyoshi Shiina, Ibaraki (JP); Hitachi Medical Corporation, Tokyo (JP)

( * ) Notice: Subject to any disclaimer, the term of this patent is extended or adjusted under 35 U.S.C. 154(b) by 263 days.

(21) Appl. No.: 12/956,959

(22) Filed: Nov. 30, 2010

(65) Prior Publication Data

US 2011/0125019 A1 May 26, 2011

Related U.S. Application Data

(62) Division of application No. 10/522,807, filed on Jan. 31, 2005, now Pat. No. 8,041,415.

(30) Foreign Application Priority Data

Jul. 31, 2002 (JP) ................................. 2002-222868
Jul. 31, 2002 (JP) ................................. 2002-222869

(51) Int. Cl.
*A61B 8/00* (2006.01)
*A61B 8/14* (2006.01)
(52) U.S. Cl. ................... 600/437; 600/442; 600/463
(58) Field of Classification Search .................. 600/433, 600/442, 463, 450, 437–447; 76/787
See application file for complete search history.

(56) References Cited

U.S. PATENT DOCUMENTS 5,462,058 A  10/1995  Yamada
5,524,636 A * 6/1996  Sarvazyan et al. ............ 600/587
6,277,074 B1  8/2001  Chaturvedi
6,638,221 B2 * 10/2003 Abe et al. ...................... 600/437
7,223,241 B2 * 5/2007  Radulescu ..................... 600/443

(Continued)

FOREIGN PATENT DOCUMENTS

DE 198 24 108 12/1999
JP 08-194822 7/1996

(Continued)

OTHER PUBLICATIONS

Makoto Yamakawa et al, "Kakucho Fukugo Jiko Sokanho ni yoru Soshiki Yugami Bunpu Suitei—Jikkenteki Kento—", Journal of Medial Ultrasonics, Apr. 15, 2001 (15.04.l01) vol. 28, No. 3, pp. J390.

(Continued)

*Primary Examiner* — Michael Rozanski
*Assistant Examiner* — Lawrence Laryea
(74) *Attorney, Agent, or Firm* — Antonelli, Terry, Stout & Kraus, LLP.

(57) ABSTRACT

An ultrasonic diagnosis system and strain distribution display method utilizing an ultrasonic probe for performing transmission/reception of ultrasonic signals to/from a subject, a storage arrangement for storing the properties of signals detected with the ultrasonic probe, a correlation computer for calculating a correlation coefficient between the properties with and without pressure applied to the subject, and a phase difference between the received signals with and without application of pressure, based upon the properties stored in the storage arrangement with and without pressure applied to the subject, a computer for calculating a displacement of each measurement point, and a strain distribution of tissue of the subject due to application of pressure, based upon the correlation coefficient and phase difference calculated by the correlation computer, and a display for displaying the strain distribution.

11 Claims, 25 Drawing Sheets

U.S. PATENT DOCUMENTS

2002/0040187 A1* 4/2002 Alam et al. .................. 600/442
2003/0149365 A1 8/2003 Torp et al.
2004/0176687 A1 9/2004 Torp et al.

FOREIGN PATENT DOCUMENTS

WO    WO 2004/010872 A1    2/2005

OTHER PUBLICATIONS

Makoto Yamakawa et al, "Tissue Elasticity Reconstruction Based on 3-Dimensional Finite-Element Model", Jpn. J. Appl. Phys., May 30, 1999, vol. 38, part 1, No. 5B, pp. 3393 to 3398.

Shiina et al "Strain Imaging using Combined RF and Envelope Autocorrelation Processing", Proceedings of the IEEE Ultrasonics Symposium 1996; vol. 2, 1996 pp. 1331-1336.

Nitta et al "Tissue Elasticity Reconstruction Based on Three-Dimensional Displacement Data Estimated by the Weighted Phase Gradient Method", 1999 IEEE Ultrasonics Symposium Proceedings International Symposium (Cat. No. 99CH37027) IEEE Piscataway, NJ USA, vol. 2, 1999 pp. 1665-1667.

Tsuyoshi Shiina et al, "Fukugo jiko solanho ni yoru jitsujikan tissue elasticity imaging/Real Time Tissue Elasticity Imaging Using The Combined Autocorrelation Method" J Med Ultrasonics, Vo. 26, No. 2, 1999, pp. 57-66 Feb. 15, 1999.

Nitta et al; Tissue Elasticity Imaging based on Combined Autocorrelation Method and 3-D Tissue Model, 1998 IEEE Ultrasonics Symposium Proceedings, Piscataway, NJ USA LNKD-DOI: 10.1109/Ultsym. 1998.176216 vol. 2, Oct. 5, 1998, pp. 1447-1450.

Nitta et al "Tissue Elasticity Reconstruction Based on Three-Dimensional Weighted Phase Gradient Method" 1999 IEEE Ultrasonics Symposium Proceedings International Symposium IEEE Piscataway, NJ UA, vol. 2 1999, pp. 1665-1668.

Tsuyoshi Shiina, et al. "Real Time Tissue Elasticity Imaging Using the Combined Autocorrelation Method," J Med Ultrasonics, vol. 26., No. 2 (1999), pp. 57-66.

Chinese Office Action dated Aug. 12, 2010, issued in corresponding Chinese Patent Application No. 200910117992.5.

Chinese Office Action dated Aug. 18, 2010, issued in corresponding Chinese Patent Application No. 200910006835.7.

Ophir, J. et al., "Elastography: A quantitative method for imaging the elasticity of biological tissues", Ultrasonic Imaging, Dynamedia Inc., Silver Spring, MD, US, vol. 13, No. 2, Apr. 1, 1991, pp. 111-134.

European Office Action dated Nov. 18, 2011, issued in corresponding European Patent Application No. 03 771 448.2.

European Office Action dated Dec. 12, 2011, issued in corresponding European Patent Application No. 10 003 297.8.

\* cited by examiner

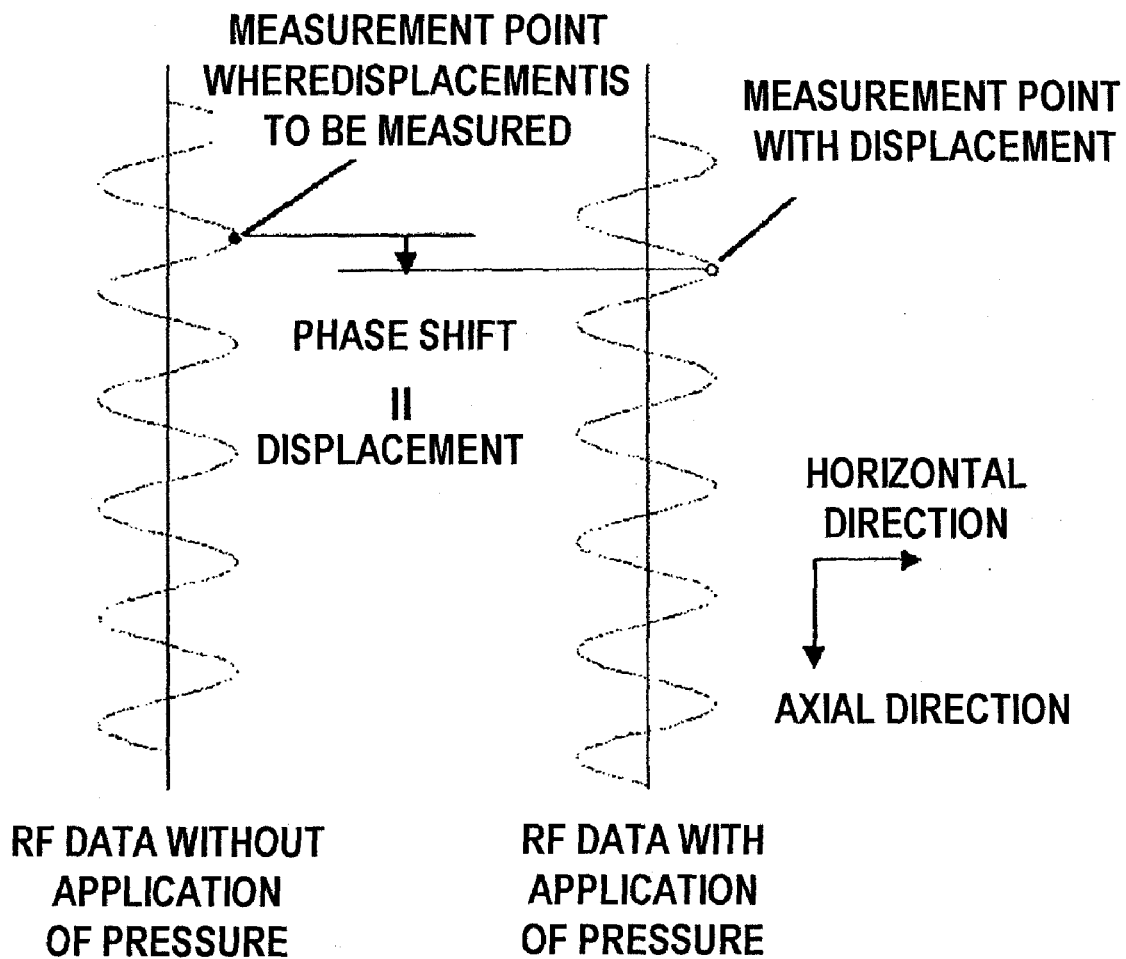

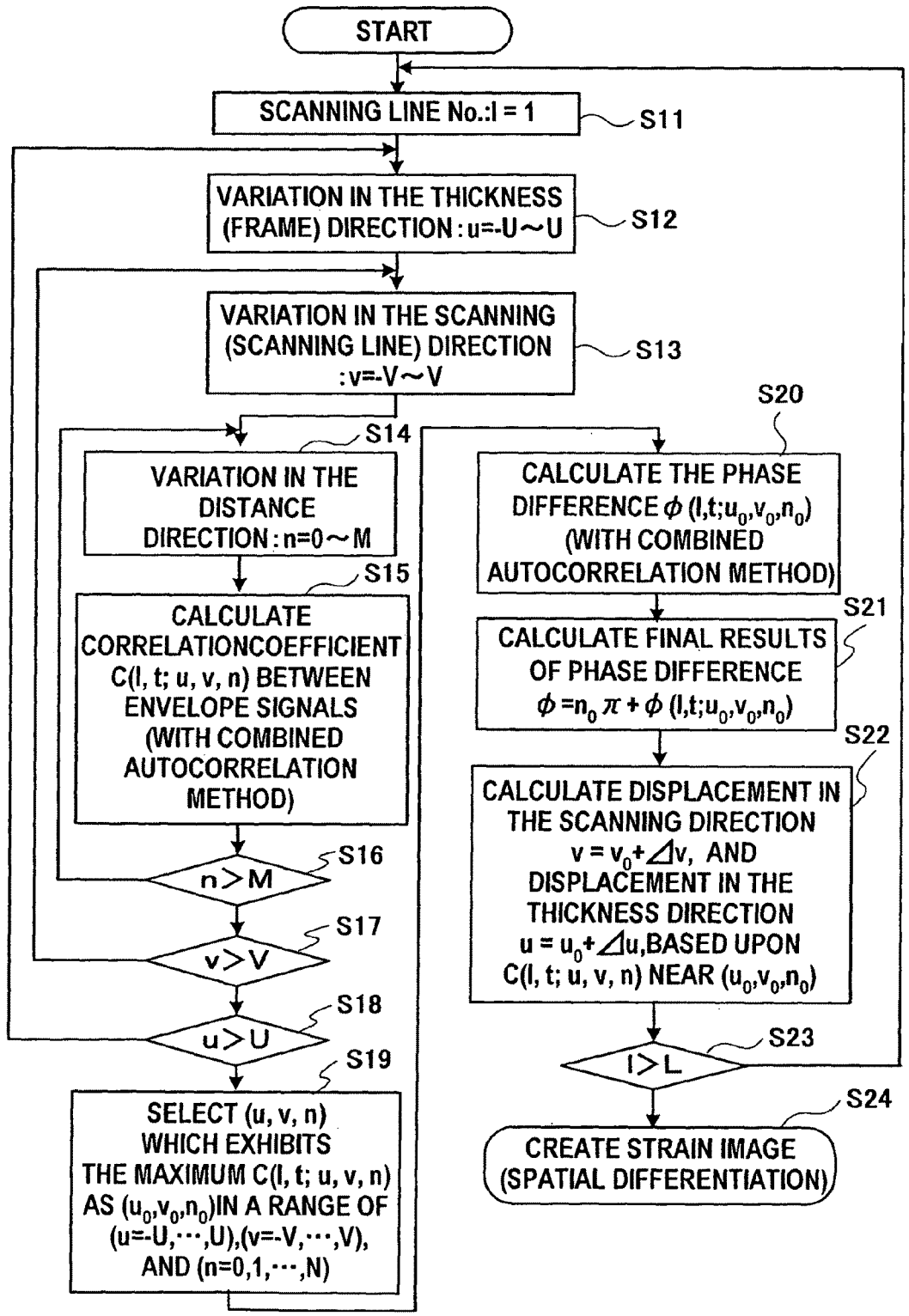

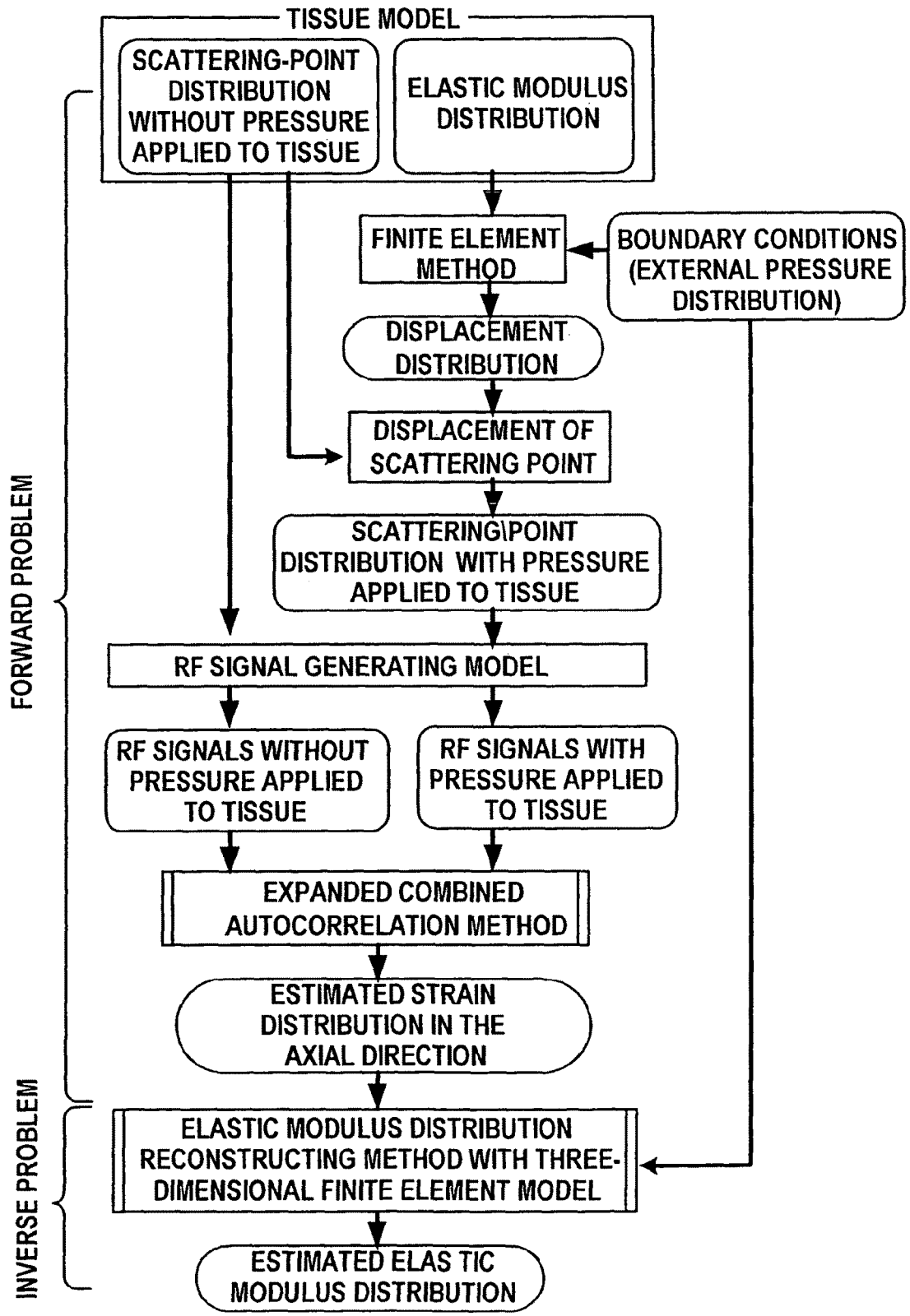

FIG. 18(A)

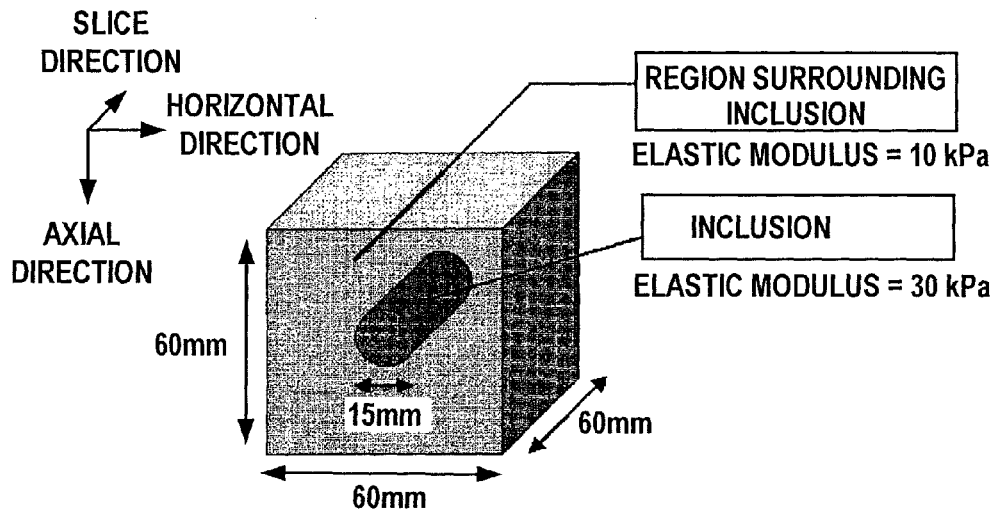

SLICE DIRECTION
HORIZONTAL DIRECTION
AXIAL DIRECTION
60mm
15mm
60mm
60mm

REGION SURROUNDING INCLUSION
ELASTIC MODULUS = 10 kPa

INCLUSION
ELASTIC MODULUS = 30 kPa

FIG. 18(B)

EXTERNAL PRESSURE OF 200 Pa IN THE AXIAL DIRECTION (UNIFORM PRESSURE APPLIED TO UPPERFACE OF MODEL)

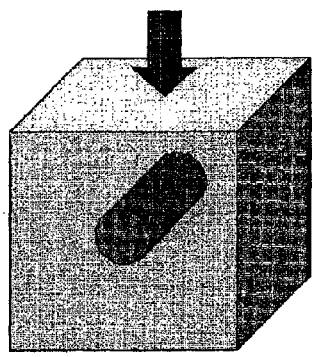

BOTTOM OF THE MODEL IS FIXED

COMPRESSION IN IN THE AXIAL DIRECTION

FIG. 18(C)

EXTERNAL PRESSURE OF 200 Pa IN THE AXIAL DIRECTION AND 30 Pa (UNIFORM PRESSURE APPLIED TO UPPERFACE OF MODEL)

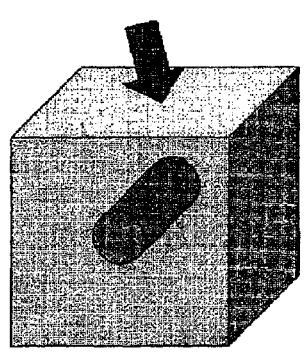

BOTTOM OF THE MODEL IS FIXED

COMPRESSION IN IN A SLANT DIRECTION

20mm

20mm

20mm

20mm

20mm

20mm

20mm

20mm

ULTRASONIC DIAGNOSIS SYSTEM AND DISTORTION DISTRIBUTION DISPLAY METHOD

CROSS REFERENCE TO RELATED APPLICATION

This application is a Divisional of U.S. application Ser. No. 10/522,807, filed Jan. 31, 2005 now U.S. Pat. No. 8,041,415, which claims priority from Japanese Patent Application Nos. JP 2002-222868 and JP 2002-222869, both filed on Jul. 31, 2002, the contents of which are incorporated herein by reference.

TECHNICAL FIELD

The present invention relates to an ultrasonic diagnosis system and a strain distribution display method which allow the user to make quantitative measurement of the rigidity of the tissue using an ultrasonic diagnosis apparatus.

BACKGROUND ART

Ultrasonic diagnosis is applied not only to observation of the tissue structure but also to the field (ultrasonic tissue characterization) where physical quantities within the tissue such as the sound speed, the damping coefficient, and so forth, are measured and furthermore, diagnosis images are created based upon the physical quantities thus measured. As a part of the field, the field is known wherein the rigidity of the tissue, i.e., the elastic property is measured. The aforementioned field is being intensely studied since the elastic property of the tissue has close relation to the pathological situation. For example, it is known that the tissue affected by: sclerosing tumors such as mammary cancer, thyroid cancer, and so forth; liver cirrhosis; arterial sclerosis; and so forth, exhibits greater rigidity than the normal tissue. Conventionally, the rigidity of the tissue is detected by touch. However, detection by touch has the disadvantage of difficulty in objective analysis, requires skill of the surgeon, and has the limitations that only the affected tissue having a certain size or more and positioned near the body surface can be detected.

On the other hand, a method is known wherein static pressure is applied to the body surface so as to compress and deform the tissue, and the strain within the tissue corresponding to the applied pressure is measured using ultrasonic wave in order to estimate the elastic property of the tissue (J. Ophir, I. Cespedes, H. Ponnekanati, Y. Yazdi, and X. Li, "Elastography: A quantitative method for imaging the elasticity of biological tissue", Ultrasonic Imaging, Vol. 13, pp. 111-134, 1991). The conventional technique has been developed based upon the fact that the tissue having great rigidity exhibits small strain thereof under pressure, and on the other hand, the tissue having small rigidity exhibits great strain thereof under pressure. That is to say, with the aforementioned conventional method, static pressure is applied to the tissue, and the elastic property of the tissue is estimated based upon the strain distribution within the tissue under pressure thus applied.

Specifically, normal measurement of ultrasonic echo signals (RF signals without application of pressure) is made using an ultrasonic diagnosis apparatus with an ultrasonic probe without pressure applied to the tissue through the ultrasonic probe. Subsequently, the surgeon applies pressure to the tissue through the ultrasonic probe to a slight degree (around several percent), following which the ultrasonic echo signals (RF signals under pressure) passing through the tissue to which pressure is applied are measured. Then, the displacement distribution which represents displacement of each point of the tissue due to the pressure thus applied is estimated based upon the RF signals with and without application of pressure of the tissue using the spatial correlation method.

The spatial correlation method has a mechanism wherein the displacement distribution within the tissue under the applied pressure is estimated based upon the RF signals (or envelope signals of the RF signals) with and without application of pressure applied to the tissue by template matching using a two-dimensional correlation function. That is to say, a two-dimensional correlation window (template) having a certain size is applied to the RF signal data corresponding to the tomographic data without pressure applied to the tissue so as to estimate displacement of a desired measurement point on the two-dimensional surface by detecting the maximum correlation between the RF signal data to which the correlation window has been applied and the RF signal data under pressure applied to the tissue using the autocorrelation processing. The aforementioned autocorrelation processing is performed for each measurement point set in the shape of a grid, for example, whereby the strain distribution is estimated. In general, the processing using the spatial correlation method is performed with poorer precision of displacement detection in the horizontal direction (scanning direction of the ultrasonic beam) than in the axial direction due to rougher sampling in the horizontal direction than in the axial direction. As described above, the spatial correlation method has the advantage of enabling the user to estimate the two-dimensional displacement vector. Furthermore, while the aforementioned spatial correlation method has the disadvantage of precision of the estimated displacement being limited by the sampling pitch, the spatial correlation method has the advantage of enabling the user to estimate the displacement distribution even in a case wherein the tissue is greatly deformed (e.g., around 5%). However, the spatial correlation method has the disadvantage of being calculation-intensive for the spatial correlation processing, leading to difficulty in processing in real time, unlike the conventional ultrasonic diagnosis.

Accordingly, it is an object of the present invention to provide a method for obtaining the displacement distribution, strain distribution, and elastic modulus distribution, in real time.

DISCLOSURE OF INVENTION

In order to solve the aforementioned problems, an ultrasonic diagnosis system according to the present invention for obtaining the displacement of the tissue of the subject based upon the reflected echo signals (RF signals) by measurement of the subject with and without application of pressure using an ultrasonic probe comprises: storage means for storing the properties of signals such as the envelope signals thereof detected with said ultrasonic probe; correlation computing means for calculating the correlation coefficient between said properties with and without pressure applied to the subject and the phase difference between the received signals with and without application of pressure, based upon said properties stored in said storage means with and without pressure applied to said subject; and displacement computing means for calculating the displacement of each measurement point due to said application of pressure based upon the correlation coefficient and the phase difference between the RF signals with and without application of pressure thus obtained by the correlation computing means. Furthermore, the ultrasonic diagnosis system according to the present invention may include strain computing means for calculating the strain distribution of the tissue of the subject by making spatial differentiation of the displacement at each measurement point, and display means for displaying the strain distribution thus obtained.

As descried above, with the ultrasonic diagnosis system according to the present invention, the displacement of each measurement point is calculated based upon the correlation between the properties such as the envelope signals with and without application of pressure, thereby enabling real-time estimation of the displacement distribution. Furthermore, with the ultrasonic diagnosis system according to the present invention, the position of each measurement point may be obtained so as to exhibit the maximum correlation coefficient between the envelope signals with and without application of pressure for the measurement points by varying said measurement points in said ultrasonic beam direction at a pitch half the wavelength of said ultrasonic signals, thereby solving a problem of aliasing which is the disadvantage in the Doppler method.

Note that the correlation computation wherein the position of each measurement point is calculated so as to exhibit the maximum correlation coefficient between the envelope signals with and without application of pressure for the measurement points by varying the phase of the envelope signals with application of pressure along the time axis so as to obtain the autocorrelation function of the envelope signals with application of pressure for each measurement point leads to great calculation time, often leading to a problem that real-time calculation cannot be made.

Accordingly, with the ultrasonic diagnosis system according to the present invention, first, the autocorrelation functions of the envelope signals with and without application of pressure are preferably calculated. Then, the correlation coefficient is obtained by varying the phase difference between the autocorrelation functions thus obtained corresponding to the predetermined variation of the measurement points, e.g., by varying the phase difference thereof at a pitch half the wavelength of the ultrasonic signals. This reduces calculation time for displacement computation, thereby enabling high-speed processing Furthermore, the ultrasonic diagnosis system according to the present invention may further include: storage means for storing the envelope signals of the quadrature-detected RF signals; correlation computing means for calculating the position of each measurement point which exhibits the maximum correlation coefficient between the envelope signals with and without application of pressure for the measurement points surrounded by a two-dimensional correlation window; and displacement computing means for obtaining at least two-dimensional displacement of each measurement point due to application of pressure based upon the position of each measurement point which exhibits the correlation coefficient and the phase difference thus obtained by the correlation computing means.

That is to say, the method which is referred to as "Combined Autocorrelation method (CA method)" is proposed in the present specification. As described above, the Combined Autocorrelation method has the advantages of two-dimensional and three-dimensional displacement measurement in the spatial correlation method with a correlation window, and the advantage of real-time and high-precision calculation in the Doppler method. The Combined Autocorrelation method allows the user to estimate the displacement distribution regardless of the displacement in the horizontal direction to a certain degree. In this case, the two-dimensional directions may comprise the ultrasonic-beam direction where the ultrasonic signals are received with the ultrasonic probe and the ultrasonic-beam scanning direction. Furthermore, with the ultrasonic diagnosis system according to the present invention, the position of each measurement point which exhibits the maximum correlation coefficient is preferably obtained by varying the measurement points in the ultrasonic-beam direction at a pitch of half the wavelength of the ultrasonic signals, and in the ultrasonic-beam scanning direction at the ultrasonic-beam pitch. Note that while the pitch at which the measurement points are varied in the ultrasonic-beam direction according to the present invention is not restricted to half of the wavelength of the ultrasonic signals, a pitch smaller than half of the wavelength of the ultrasonic signals is preferably employed.

In order to further improve calculation speed of the displacement computation, first, the autocorrelation functions of the envelope signals with and without application of pressure are preferably calculated. Then, the position of each measurement point which exhibits the maximum correlation coefficient is obtained by varying the phase difference between the autocorrelation functions in a range corresponding to the predetermined variation of the measurement points.

Furthermore, the displacement computation according to the present invention may be applied not only to two-dimensional calculation, but also to three-dimensional calculation. With an three-dimensional arrangement employing an ultrasonic probe having a one-dimensional array structure, the frame data stored in the storage means comprises volume data formed of multiple frame data sets each of which serves as slice data. On the other hand, with an three-dimensional arrangement employing an ultrasonic probe having a two-dimensional array structure, the data contains the envelope signals obtained by scanning in the slice direction. The correlation computing means obtain the position of each measurement point which exhibits the maximum correlation coefficient between the envelope signals with and without application of pressure for the measurement points surrounded by a three-dimensional correlation window by varying the measurement points surrounded by the three-dimensional correlation in three-dimensional directions as to the volume data. At the same time, the correlation computing means calculate the phase difference between the RF signals with and without application of pressure. In this case, the three-dimensional directions may comprise the ultrasonic-beam direction where the ultrasonic signals are received with the ultrasonic probe, the ultrasonic-beam scanning direction, and the slice direction orthogonal to the aforementioned two directions. Furthermore, the correlation computing means preferably obtain the phase difference between the RF signals with and without application of pressure in the ultrasonic-beam direction, in the ultrasonic-beam scanning direction, and in the slice direction orthogonal to the aforementioned two directions. Furthermore, the high-speed processing method described above may be applied to an three-dimensional arrangement. Furthermore, the calculation described above may be made by varying the measurement points in the slice direction in units of the slice pitch of the ultrasonic beam.

Furthermore, an method for obtaining the elastic modulus distribution according to the present invention may include elastic modulus computation means for creating at least a two-dimensional or three-dimensional finite element model by dividing the subject into a finite number of elements, and computing the elastic modulus distribution based upon the information used for creating the model and the strain distribution thus obtained. Furthermore, the elastic modulus distribution thus obtained may be displayed with the display means. In this case, the elastic modulus computing means preferably create a three-dimensional finite element model by dividing the tissue of the subject into a finite number of rectangular parallelepiped elements on the assumption that the tissue of the subject exhibits isotropic elasticity and near-incompressibility. Furthermore, the elastic modulus computing means preferably compute the elastic modulus distribution based upon the information regarding the aforementioned strain distribution using the elastic equation on the assumption that the tissue of the subject exhibits the uniform elastic modulus, the uniform stress, and the uniform strain, for each element.

As described above, calculation according to the present invention is made on the assumption that the tissue exhibits isotropic elasticity. The reason is that the relation between the stress and strain exhibits near-linearity under static external pressure applied to the tissue. Accordingly, approximate calculation can be made on the assumption that the tissue serves as an elastic model. In addition, the tissue exhibits isotropic properties, and accordingly, calculation according to the present invention may be made on the assumption that the tissue serves as an isotropic elastic model. On the other hand, with the present invention, calculation is made on the assumption that the tissue exhibits near-incompressibility. The reason is that if calculation is made on the assumption that the tissue exhibits the complete incompressibility, i.e., calculation is made with the constant Poisson's ratio of 0.5 within the tissue, the elastic equation becomes a special case, leading to a problem that calculation cannot be made using the finite element method. Note that with the present invention, calculation may be made with a uniform Poisson's ratio within the tissue. In this case, only the Young's modulus should be estimated for estimation of the elastic modulus distribution, thereby reducing the inverse problem. Note that the Poisson's ratio exhibits sufficient uniformity within the tissue, and accordingly, with the present invention, calculation is preferably made with the Poisson's ratio of 0.49. The elastic modulus distribution computation according to the present invention enables reconstruction of the elastic modulus distribution based upon the strain distribution in the axial direction alone which can be computed with high precision, thereby enabling stable computation of the elastic modulus distribution.

BRIEF DESCRIPTION OF THE DRAWINGS

FIG. 4 is a diagram which shows the mechanism of the Doppler method.

FIG. 9 is a flowchart which shows the basic algorithm of the three-dimensional combined autocorrelation method employed in the ultrasonic diagnosis system according to the present invention, and a part of the processing shown in FIG. 7 in detail.

FIG. 12 is a schematic diagram which shows the procedure of simulation.

FIG. 18 is a schematic diagram which shows a tissue model used for simulation of compression in a slant direction.

BEST MODE FOR CARRYING OUT THE INVENTION

Description will be made below regarding an ultrasonic diagnosis system according to an embodiment of the present invention with reference to the accompanying drawings. An ultrasonic diagnosis system according to the present embodiment employs a method which is referred to as "expanded combined autocorrelation method" wherein the processing for one-dimensional detection by correlation calculation based upon the envelope signals using the combined autocorrelation method through a one-dimensional window is expanded to handle the displacement in the horizontal direction by two-dimensional detection through a two-dimensional correlation window. Furthermore, with the expanded combined autocorrelation method according to the present embodiment, envelope-correlation calculation is performed for only the grid points set with a pitch of half the wavelength of the ultrasonic wave in the axial direction, and with the beam-line pitch in the horizontal direction for reduction of calculation amount, thereby enabling high-speed calculation. Note that the expanded combined autocorrelation method according to the present embodiment employs the phase information in the same way as with the combined autocorrelation method for improving the precision of the estimated displacement in the axial direction. However, the phase information is not employed for estimating displacement in the horizontal direction due to lack of the signals serving as a carrier. Accordingly, the precision of the estimated displacement in the horizontal direction is limited corresponding to the sampling pitch (ultrasonic-wave beam-line pitch) as with the spatial correlation method. Note that the expanded combined autocorrelation method according to the present embodiment has no particular mechanism for improving the precision of the estimated displacement in the horizontal direction since the elastic modulus distribution can be estimated based upon the strain (displacement) distribution in the axial direction alone using the elastic modulus distribution reconstructing method described later.

Figure 1:
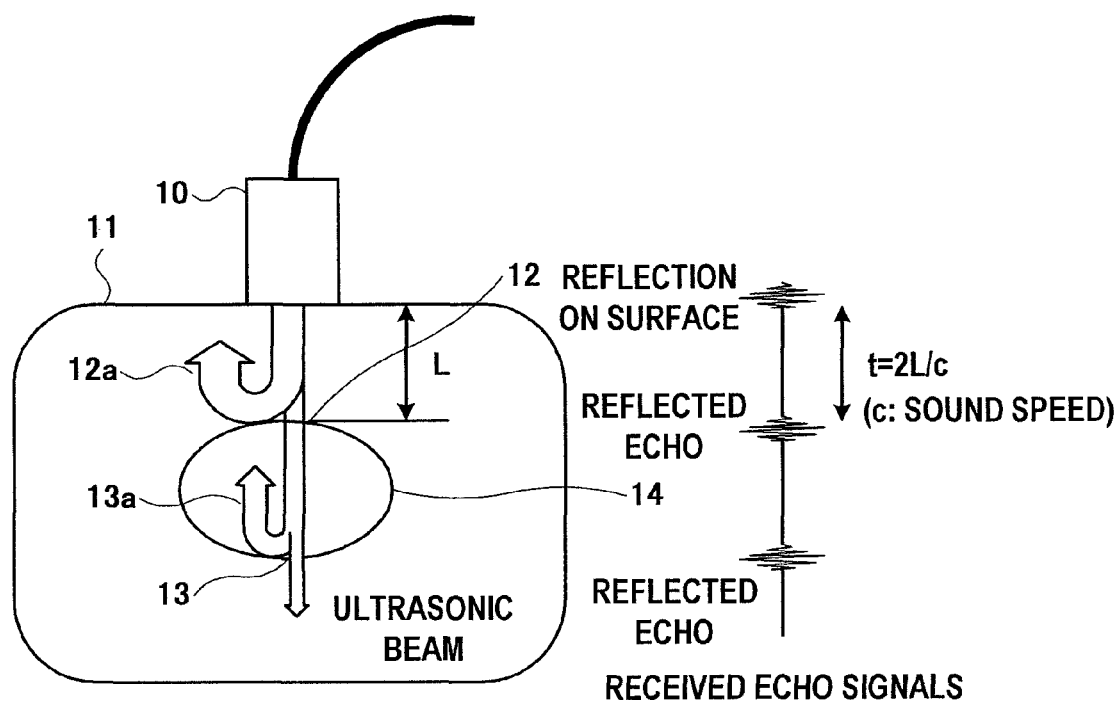
FIG. 1 is a diagram for describing the mechanism of an ultrasonic diagnosis apparatus.

Before description of a specific configuration of the expanded combined autocorrelation method according to the present embodiment, description will be made regarding the combined autocorrelation method which is the basis of the expanded combined autocorrelation method according to the present invention with reference to FIG. 1 through FIG. 6. FIG. 1 is a diagram for describing a mechanism of an ultrasonic diagnosis apparatus. As can be clearly understood from the drawing, an ultrasonic probe 10 serving as an ultrasonic detector has functions for converting electric signals to an ultrasonic wave and converting an ultrasonic wave into electric signals, which allows the user to cast ultrasonic pulse signals toward the tissue 11. A part of the ultrasonic pulse signals passing through the tissue 11 is reflected at a first boundary 12 between the regions having acoustic impedance different one from another. The reflected ultrasonic wave which will be referred to as "reflected echo signals 12a" passes through the tissue toward the ultrasonic probe 10, and the other ultrasonic wave passes through the first boundary 12. A part of the ultrasonic pulse signals passing through the first boundary 12 is reflected at a second boundary 13 between the regions having acoustic impedance different one from another. In the same way, the ultrasonic pulse signals reflected at the second boundary 13 which will be referred to as "reflected echo signals 13a" passes through the tissue toward the ultrasonic probe 10, and on the other hand, the other ultrasonic pulse signals passes through the second boundary 13. The reflected ultrasonic echo signals are received by the ultrasonic probe 10 so as to be converted into reflected echo signals which are electric signals. In this case, the period of time t from casting of the ultrasonic pulse signals from the ultrasonic probe 10 up to reception of the echo signals reflected from a reflecting object 14 (boundary between the regions having acoustic impedance different one from another) positioned away from the ultrasonic probe 10 by the distance L is represented by the following Expression (1).

$$t = \frac{2L}{c} \quad (1)$$

Here, c represents the sound speed within the tissue, and can be determined to be a constant at around 1500 [m/second] through soft tissue. Accordingly, the distance L between the probe and the reflecting object is calculated based upon the time t from casting of the ultrasonic wave up to reception of the reflected echo signals. Furthermore, the reflected echo signals have information with regard to the acoustic properties of the tissue, and accordingly, images of the tissue information such as B-mode tomographic images can be displayed on a monitor based upon the reflected echo signals.

For example, a method is known wherein the elastic properties which represent the rigidity of the tissue are measured using an ultrasonic diagnosis apparatus. The aforementioned method for measuring the elastic properties has a mechanism wherein mechanical vibration is applied to the tissue, and the rigidity information is estimated based upon the propagating speed of the transverse wave thus generated, based upon the fact that the transverse wave passes through rigid tissue at a high propagating speed and passes through soft tissue at a low propagating speed. Strictly, the propagating speed v of the transverse wave which propagates through the tissue is dependent upon the density of the tissue ρ, the shear modulus $\mu_1$, shear viscosity $\mu_2$, and the angular frequency of the vibration ω, as represented by the following Expression (2).

$$v = \sqrt{\frac{2(\mu_1^2 + \omega^2 \mu_2^2)}{\rho(\mu_1 + \sqrt{\mu_1^2 + \omega^2 \mu_2^2})}} \quad (2)$$

Figure 2A:
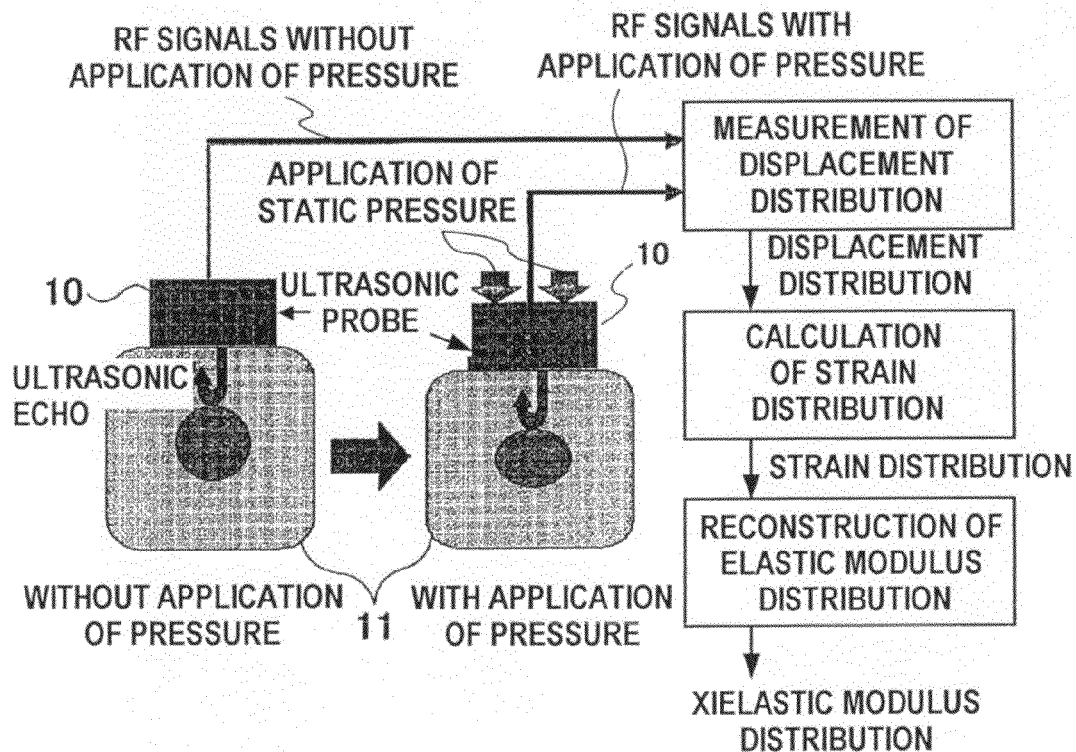
FIG. 2 is a diagram which shows a specific example of a tissue elasticity measurement method by application of static pressure, and the mechanism of the tissue elasticity measurement method by application of static pressure.
Figure 2B:
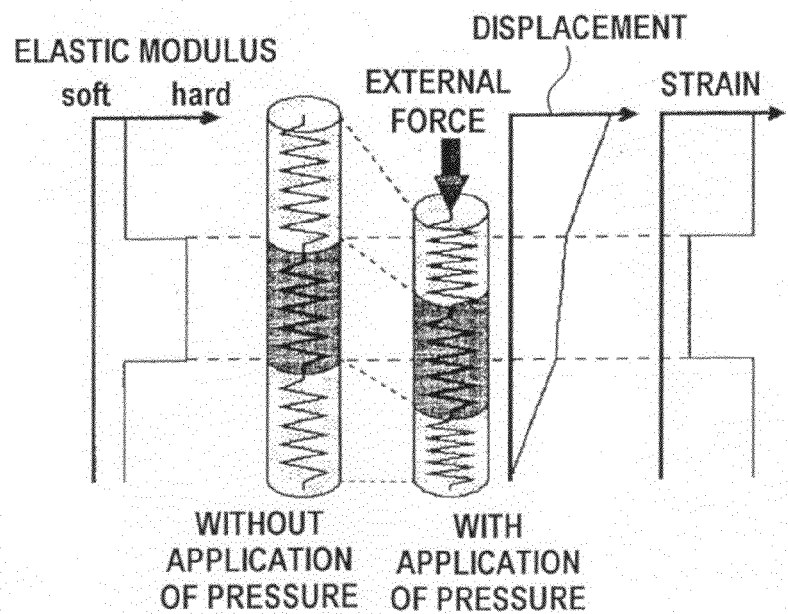

On the other hand, as shown in FIG. 2, a method has been proposed wherein static pressure is applied to the tissue, and the elastic properties of the tissue are estimated based upon the strain distribution thereof under the applied pressure. The aforementioned method has been developed based upon the fact that such static pressure causes small strain within rigid tissue, and causes great strain within soft tissue. FIG. 2(A) is a diagram which shows a specific example of a tissue-elasticity measuring method with application of static pressure. FIG. 2(B) is a diagram which shows the mechanism of the tissue elasticity measuring method with application of static pressure. As can be clearly understood from the drawings, with the aforementioned method, normal measurement of the ultrasonic echo signals (RF signals without application of pressure) is made for the tissue 11 without application of pressure using a conventional ultrasonic diagnosis apparatus with the ultrasonic probe 10. Subsequently, the tissue 11 is pressed to a slight degree (around several percent) through the ultrasonic probe 10, and measurement of the ultrasonic echo signals (RF signals with application of pressure) is made for the tissue 11 under the applied pressure. Then, the displacement distribution which represents the displacement of each point within the tissue under pressure is estimated based upon the RF signals measured with and without pressure applied to the tissue. The principal examples of the displacement-distribution estimating methods include a method using spatial correlation, and a method using the Doppler effect.

Figure 3:
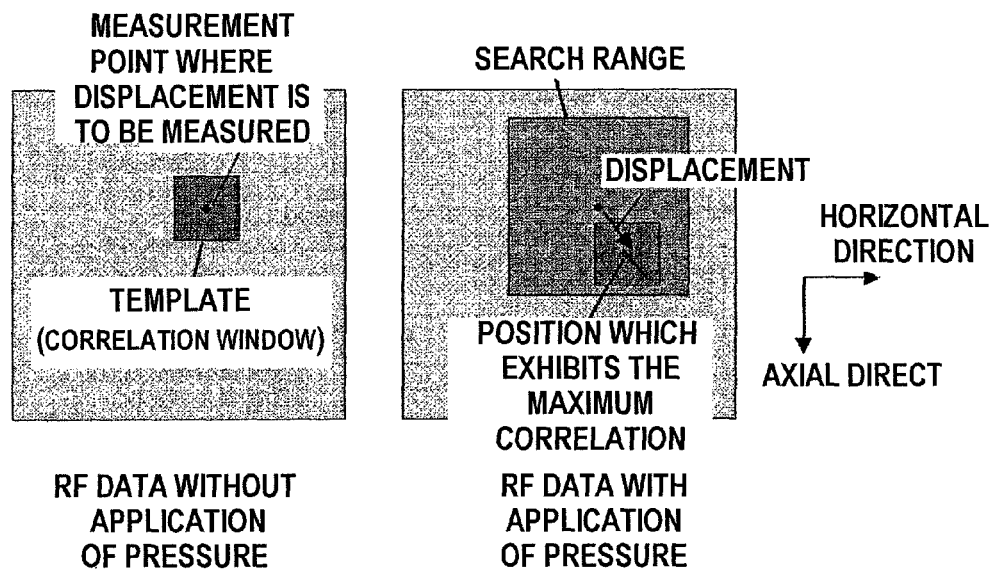
FIG. 3 is a diagram which shows the mechanism of the spatial correlation method.
Figure 8:
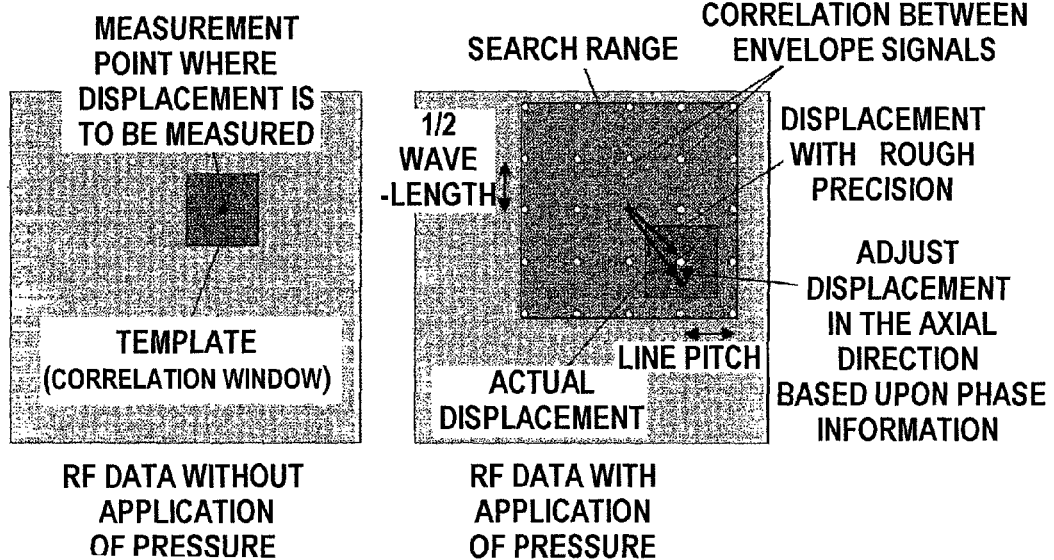
FIG. 8 is a flowchart which shows basic algorithm of the three-dimensional combined autocorrelation method.

FIG. 3 is a diagram which shows a mechanism of the spatial correlation method. With the present method, the strain distribution within the tissue under the applied pressure is estimated based upon the RF signals (or envelope signals of the RF signals) with and without pressure applied to the tissue by template matching using a two-dimensional correlation function. Description will be made below regarding specific processing thereof. First, with the RF signals (or envelope signals thereof) with and without pressure applied to the tissue as $i_1$(t, x) and $i_2(t, x)$, respectively, the cross-correlation coefficient $C(t, x; n, m)$ between the aforementioned two signals is represented by the following Expression (3).

$$C(t, x; n, m) = \frac{\sum_{v=-t_0/2}^{t_0/2} \sum_{w=-x_0/2}^{x_0/2} i_1(t+v, x+w) i_2(t+v+nL_t, x+w+mL_x)}{\sqrt{\sum_{v=-t_0/2}^{t_0/2} \sum_{w=-x_0/2}^{x_0/2} i_1^2(t, x)} \cdot \sqrt{\sum_{v=-t_0/2}^{t_0/2} \sum_{w=-x_0/2}^{x_0/2} i_2^2(t+v+nL_t, x+w+mL_x)}} \quad (3)$$

Here, t represents the coordinate point in the ultrasonic-wave beam direction (axial direction), x represents the coordinate point orthogonal thereto (in the horizontal direction), t0 represents the correlation-window size in the axial direction, x0 represents the correlation-window size in the horizontal direction, $L_t$ represents the sampling pitch in the axial direction, and $L_x$ represents the sampling pitch in the horizontal direction. Furthermore, n and m represent integers. In this case, with the combination (n, m) of the cross-correlation coefficient which exhibits the maximum value as (k, l), the displacement $u_y$ in the axial direction and the displacement $u_x$ in the horizontal direction at the measurement point (t, x) are represented by the following Expressions, respectively.

$$u_y = kL_t$$

$$u_x = lL_x$$

Note that data sampling is made at a rougher sampling pitch Lx in the horizontal direction than the sampling pitch Lt in the axial direction, leading to poorer precision of the displacement detection in the horizontal direction than in the axial direction. The aforementioned processing is made for each measurement point, whereby displacement distribution is estimated. The spatial correlation method has the advantage of enabling the user to estimate two-dimensional displacement vector components. Furthermore, the spatial correlation method allows the user to estimate the displacement distribution even if great strain (around 5%) occurs in the tissue. However, the aforementioned method leads to a great amount of calculation, leading to difficulty in calculation in real time, unlike the conventional ultrasonic measurement systems. Furthermore, the precision of estimated displacement is limited by the sampling pitch, thereby leading to a problem of relatively poor precision as compared with the Doppler method which will be described later.

FIG. 4 is a diagram which shows a mechanism of the Doppler method. With the present method, the displacement distribution within the tissue under the applied pressure is estimated based upon the RF signals with and without pressure applied to the tissue using the Doppler effect which is also employed in blood flow measurement.

Description will be made below regarding specific processing. First, the RF signals with and without pressure applied to the tissue are represented by models as represented by the following Expression (4).

$$i_1(t) = Re[A(t)e^{-j(\omega_0 t - \theta)}]$$

$$i_2(t) = Re[A(t-\tau)e^{-j[\omega_0(t-\tau)-\theta]}] \quad (4)$$

Here, $i_1(t)$ represents the RF signals without application of pressure, $i_2(t)$ represents the RF signals with application of pressure, A(t) represents the envelope signals, $\omega_0$ represents the center angular frequency of the ultrasonic wave, and $\tau$ represents the time shift. Upon performing quadrature detection for each of two RF signals, the base-band signals are obtained as represented by the following Expression.

$$s_1(t) = A(t)e^{j\theta}$$

$$s_2(t) = A(t-\tau)e^{j(\omega_0 \tau + \theta)} \quad (5)$$

Also, the complex correlation function $R_{12}(t)$ between the aforementioned two signals is represented by the following Expression.

$$R_{12}(t) = \int_{-t_0/2}^{t_0/2} s_1(t+v) s_s(t+v) \ast dv = R_A(t) e^{-j\omega_0 \tau} \quad (6)$$

Here, $R_A(t)$ represents the autocorrelation function of the envelope signals, and $t_0$ represents the correlation window size in the ultrasonic-beam axial direction. Furthermore, the asterisk "*" represents a complex conjugate operator. Accordingly, the time shift $\tau$ and the displacement $u_y$ in the axial direction due to application of pressure are obtained from the phase $\phi(t)$ of the correlation function $R_{12}(t)$ as represented by the following Expression (7).

$$\tau = -\frac{\phi(t)}{\omega_0}$$

$$u_y = \frac{c\tau}{2} \quad (7)$$

Note that c represents the sound speed within the tissue, and is assumed to be constant within the tissue.

With the Doppler method, the aforementioned processing is performed for each measurement point, and the displacement distribution is estimated in the same way as with the blood flow measurement developed based upon the Doppler effect. Thus, the Doppler method has the advantage of real-time measurement. Furthermore, the Doppler method makes calculation using the phase information, thereby estimating the displacement with higher precision than with the spatial correlation method. However, the Doppler method has the disadvantage that measurement of large displacement, e.g., displacement of a quarter or more the wavelength of the ultrasonic-wave center frequency leads to aliasing, resulting in a problem that correct displacement cannot be estimated. Furthermore, the Doppler method has the disadvantage that displacement other than that in the axial direction cannot be estimated as can be understood from the above Expression.

Figure 5:
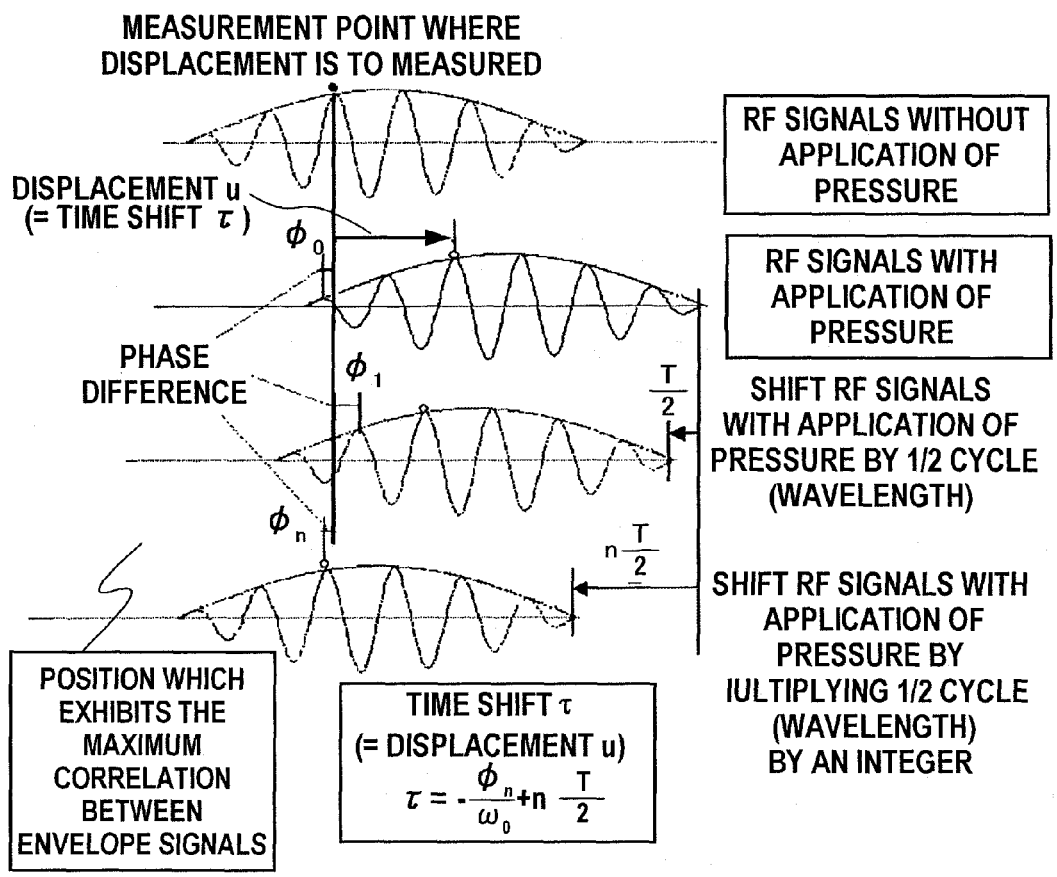
FIG. 5 is a diagram which shows the mechanism of the combined autocorrelation method.

In order to solve the aforementioned problems, the present inventors have proposed "Combined Autocorrelation Method (CA method)" having the advantages of both of the aforementioned two methods. FIG. 5 is a diagram which shows a mechanism of the combined autocorrelation method proposed by the present inventors. With the combined autocorrelation method, calculation is made using correlation of the envelope signals of the RF signals, thereby solving a problem of aliasing which is the disadvantage in the Doppler method. Description will be made below regarding specific processing.

First, the RF signals with and without pressure applied to the tissue are represented by models as represented by the following Expression in the same way as with the Doppler method.

$$i_1(t) = Re[A(t)e^{-j(\omega_0 t - \theta)}]$$

$$i_2(t) = Re[A(t-\tau)e^{-j[\omega_0(t-\tau)-\theta]}] \quad (8)$$

Here, $i_1(t)$ represents the RF signals without application of pressure, $i_2(t)$ represents the RF signals with application of pressure, $A(t)$ represents the envelope signals, $\omega_0$ represents the center angular frequency of the ultrasonic wave, and $\tau$ represents the time shift. Upon performing quadrature detection for each of two RF signals, the base-band signals are obtained as represented by the following Expression.

$$s_1(t)=A(t)e^{j\theta}$$

$$s_2(t)=A(t-\tau)e^{j(\omega_0\tau+\theta)} \quad (9)$$

Then, the complex correlation function $R_{12}(t; n)$ between the aforementioned two signals is represented by the following Expression.

$$R_{12}(t;n) = \int_{-t_0/2}^{t_0/2} s_1(t+v)s_2\left(t+n\frac{T}{2}+v\right)^* dv \quad (10)$$

$$= R_A\left(t;\tau-n\frac{T}{2}\right)e^{-j\omega_0\left(\tau-n\frac{T}{2}\right)}$$

$$(n = \ldots, -2, -1, 0, 1, 2, \ldots)$$

Here, T represents the cycle of the ultrasonic wave, $R_A(t;\tau)$ represents the autocorrelation function of the envelope signals, and $t_0$ represents the correlation window size. Furthermore, the asterisk "*" represents a complex conjugate operator. Here, n represents the variable number, and each calculation is made for different n; displacement at each measurement point being calculated around the point determined by the variation number. Note that in a case of n=0, the combined autocorrelation function matches the autocorrelation function in the Doppler method as represented by the Expression (6). That is to say, the combined autocorrelation function with n of 0 leads to a problem of aliasing in a case wherein measurement is made for displacement of a quarter or more the wavelength of the ultrasonic wave. In order to solve the aforementioned problem, with the combined autocorrelation method, the envelope correlation coefficient $C(t; n)$ is defined as represented by the following Expression (11).

$$C(t;n) = \frac{|R_{12}(t;n)|}{\sqrt{|R_{11}(t;0)|\cdot|R_{22}(t;n)|}} \quad (11)$$

Note that $R_{11}(t; 0)$ represents the autocorrelation function of $s_1(t)$, and $R_{22}(t; n)$ represents the autocorrelation function of $s_2(t+nT/2)$. With n of the envelope correlation coefficient $C(t; n)$ which exhibits the maximum value as k, calculation is made using the phase $\phi$ of $R_{12}(t; k)$ with n=k. In this case, displacement is calculated without aliasing. The reason is that calculation of the envelope correlation is made at a pitch of half the wavelength. Note that the calculation pitch of half the wavelength is the maximum pitch for calculating displacement while preventing aliasing. Thus, the time shift $\tau$ and the displacement $u_y$ in the axial direction are calculated using $\phi(t; k)$ as represented by the following Expression.

$$\tau = -\frac{\phi(t;k)}{\omega_0} + k\frac{T}{2} \quad (12)$$

$$u_y = \frac{c\tau}{2}$$

Note that c represents the sound speed within the tissue, and is assumed to be constant within the tissue.

With the combined autocorrelation method, the aforementioned processing is performed for each measurement point, whereby displacement distribution is estimated, which is an expanded method of the Doppler method. Thus, the combined autocorrelation method has the advantage of real-time measurement. Furthermore, the combined autocorrelation method has the advantage of enabling the user to estimate the displacement distribution containing large displacement (i.e., displacement of a quarter or more the wavelength of the ultrasonic wave) using envelope correlation, unlike the Doppler method.

Figure 6:
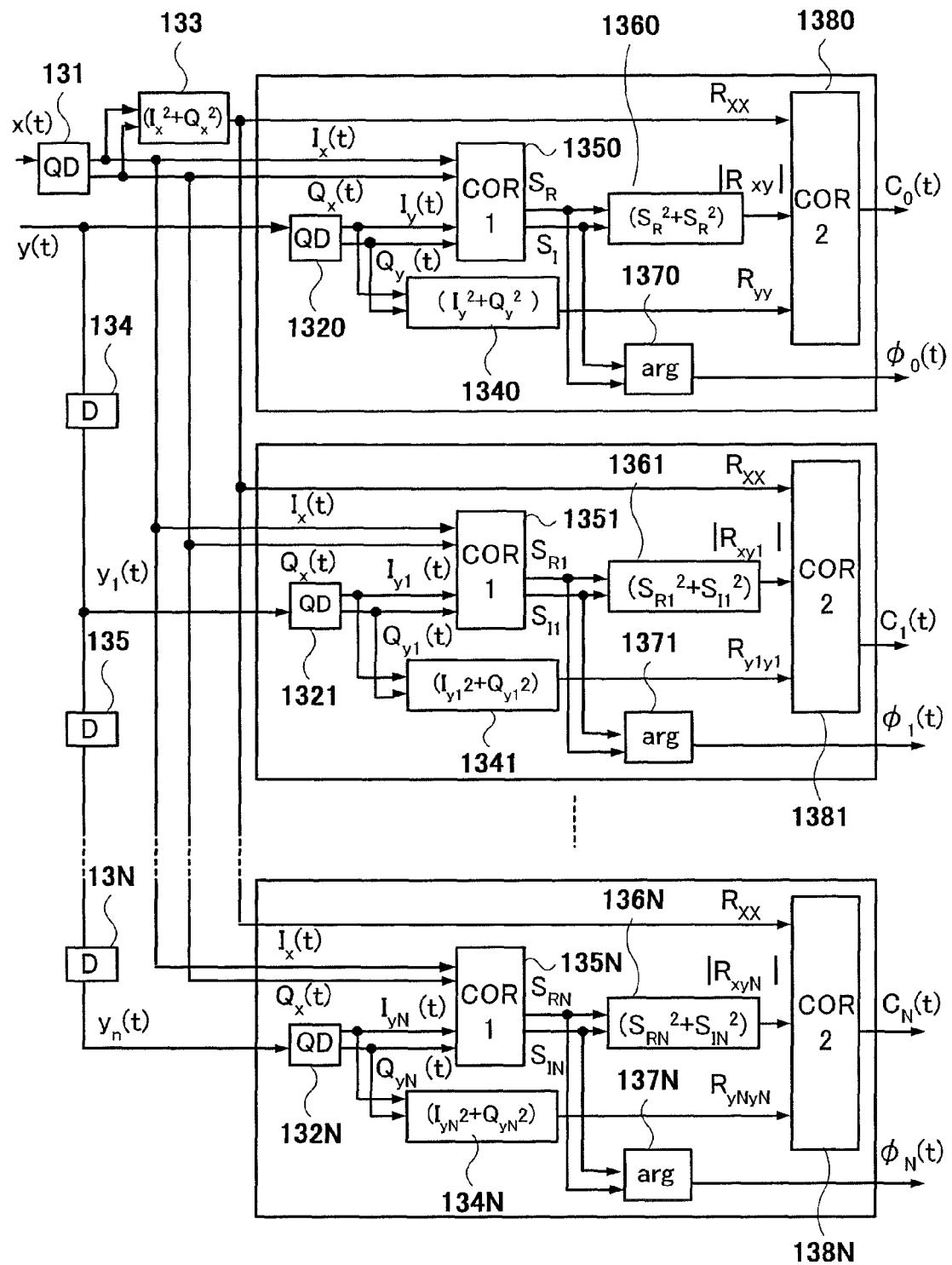
FIG. 6 is a block diagram which shows a circuit configuration for executing basic algorithm of the combined autocorrelation method.

FIG. 6 is a block diagram which shows a circuit configuration for performing basic algorithm of the combined autocorrelation method. In the drawing, echo signals x(t) obtained without application of pressure are input to a unpressed quadrature detection circuit (QD) 131 for quadrature detection, and the quadrature-detected signals Ix(t) and Qx(t) thus detected are input to a first correlation computing circuit 133 and first correlation coefficient computing circuits 1350 through 135N. On the other hand, echo signals y(t) obtained under the applied pressure are input to a first pressed quadrature detection circuit (QD) 1320 for quadrature detection, and the quadrature-detected signals Y(t)=Iy+jQy(Iy(t), Qy(t)) thus detected are input to a first correlation coefficient computing circuit 1340 and the second correlation computing circuit 1350. A first delay circuit 134 delays the echo signals y(t) by the cycle period T of the ultrasonic wave, and the delayed echo signals y1=y(t−T) are input to a second pressed quadrature detection (QD) circuit 1321. In the same way, a second delay circuit 135 delays the echo signals y1=y(t−T) which have been delayed by the first delay circuit 134 by the cycle period T of the ultrasonic wave, and the delayed echo signals y2=y(t−2T) are input to a next second pressed quadrature detection (QD) circuit 1322 (not shown). Note that the circuit has N delay circuits, and the echo signals are consecutively delayed, and the echo signals delayed by a value obtained by multiplying the cycle period T by an integer are input to the corresponding pressed quadrature detection circuit in the same way.

The first correlation computing circuit 133 computes a correlation value Rxx based upon the signals Ix and Qx, and outputs the correlation value Rxx to second correlation coefficient computing circuits 1380 through 138N. The second correlation computing circuit 1340 receives the quadrature-detected signals Iy(t) and Qy(t) from the pressed quadrature detection circuit 1320, computes a correlation value Ryy based upon the signals Iy and Qy, and outputs the correlation value Ryy to the second correlation computing circuit 1380. The first correlation coefficient computing circuit 1350 receives the quadrature-detected signals Ix(t) and Qx(t) from the unpressed quadrature detection circuit 131, and the quadrature-detected signals Iy(t) and Qy(t) from the first pressed quadrature detection circuit 1320, calculates the complex base-band signals $S_R$ and $S_I$ based thereupon, and outputs the base-band signals $S_R$ and $S_I$ to a third correlation computing circuit 1360 and a phase-difference computing circuit 1370. The third correlation computing circuit 1360 receives the complex base-band signals $S_R$ and $S_I$ from the first correlation coefficient computing circuit 1350, calculates the correlation value |Rxy| based thereupon, and outputs the calculated correlation value |Rxy| to the second correlation coefficient computing circuit 1380. The phase-difference computing circuit 1370 receives the complex base-band signals $S_R$ and $S_I$ from the first correlation coefficient computing circuit 1350, and calculates the phase difference $\phi_0(t)$ based thereupon. The second correlation coefficient computing circuit 1380 receives the correlation value Rxx from the first correlation computing circuit 133, the correlation value $|Rxy|$ from the third correlation computing circuit 1360, and the correlation value $Ryy$ from the second correlation computing circuit 1340, computes the correlation coefficient $C_0(t)$ based upon the aforementioned correlation values, and outputs the calculated correlation coefficient $C_0(t)$.

The second pressed quadrature detection circuit (QD) 1321 receives the echo signals $y_1=y(t-T)$ delayed by the first delay circuit 134, and outputs the quadrature-detected signals $Y_1(t)=Iy_1+jQy_1(Iy_1(t), Qy_1(t))$ to a first correlation coefficient computing circuit 1341 and a second correlation computing circuit 1351. The second correlation computing circuit 1341 receives the quadrature-detected signals $Iy_1(t)$ and $Qy_1(t)$ from the second pressed quadrature detection circuit (QD) 1321, computes a correlation value $Ry_1y_1$ based upon the signals $Iy_1(t)$ and $Qy_1(t)$, and outputs the correlation value $Ry_1y_1$ to a second correlation computing circuit 1381. The first correlation coefficient computing circuit 1351 receives the quadrature-detected signals $Ix(t)$ and $Qx(t)$ from the unpressed quadrature detection circuit 131, and the quadrature-detected signals $Iy_1(t)$ and $Qy_1(t)$ from the second pressed quadrature detection circuit (QD) 1321, calculates the complex base-band signals $S_{R1}$ and $S_{I1}$ based thereupon, and outputs the base-band signals $S_{R1}$ and $S_{I1}$ to a third correlation computing circuit 1361 and a phase-difference computing circuit 1371. The third correlation computing circuit 1361 receives the complex base-band signals $S_{R1}$ and $S_{I1}$ from the first correlation coefficient computing circuit 1351, calculates the correlation value $|Rxy_1|$ based thereupon, and outputs the calculated correlation value $|Rxy_1|$ to the second correlation coefficient computing circuit 1381. The phase-difference computing circuit 1371 receives the complex base-band signals $S_{R1}$ and $S_{I1}$ from the first correlation coefficient computing circuit 1351, and calculates the phase difference $\phi_1(t)$ based thereupon. The second correlation coefficient computing circuit 1381 receives the correlation value $Rxx$ from the first correlation computing circuit 133, the correlation value $|Rxy_1|$ from the third correlation computing circuit 1361, and the correlation value $Ry_1y_1$ from the second correlation computing circuit 1341, computes the correlation coefficient $C_1(t)$ based upon the aforementioned correlation values, and outputs the calculated correlation coefficient $C_1(t)$.

In the same way, each of the second pressed quadrature-detection circuit (QD) 1322 through 132N which receive the signals from the corresponding delay circuit downstream from the first delay circuit 135, each of the second correlation computing circuits 1342 through 134N, each of the first correlation coefficient computing circuits 1352 through 135N, each of the third correlation circuits 1362 through 136N, each of the phase-difference computing circuits 1372 through 137N, and each of the second correlation coefficient computing circuits 1382 through 138N, perform the same processing as with the first-stage and second-stage circuit components as described above, whereby the correlation coefficients $C_2(t)$ through $C_N(t)$, and the phase values $\phi_2(t)$ through $\phi_N(t)$ are output. As described above, the circuit for performing the basic algorithm of the combined autocorrelation method shown in FIG. 6 has a configuration wherein the echo signals $y(t)$ under the applied pressure are delayed by a period of half the cycle period $T/2$ of the ultrasonic wave (half the wavelength) for each of the delay circuits 134 through 13N, and each of the echo signals thus delayed are quadrature-detected by the corresponding quadrature-detection circuit (QD) 1320 through 132N.

As described above, the strain distribution is obtained by spatial differentiation of the estimated displacement distribution under the pressure applied to the tissue. The strain distribution represents the relative elastic property of the tissue, and accordingly, diagnosis based upon the strain distribution exhibits effects similar to those of the diagnosis based upon the elastic modulus distribution. However, in a case of liver cirrhosis which causes rigidity of the entire affected tissue, it is difficult to make the same diagnosis of the tissue as with the elastic-property distribution which allows the surgeon to make quantitative estimation. Accordingly, in recent years, reconstruction methods for tissue elastic modulus distribution are being studied. Note that all of these reconstruction methods are in the research stage, and that no standard method has been established.

On the other hand, the tissue elastic modulus distribution can be obtained based upon the strain distribution and the stress distribution within the tissue as described above. However, it is difficult to make direct measurement of the stress distribution with the existing technique. Accordingly, in practicality, the elastic modulus distribution is reconstructed based upon the strain distribution so as to satisfy the boundary conditions under the pressure applied to the tissue, i.e., there is the need to solve the inverse problem. In general, it is difficult to solve the inverse problem, and few elastic modulus reconstruction methods have been proposed. Description will be made regarding the conventional elastic modulus reconstruction methods.

First, a method is known, which has been proposed on the assumption that the tissue is represented by a one-dimensional model (one-dimensional elastic model). That is to say, a method is known wherein the elastic modulus distribution is calculated on the assumption that the tissue is represented by a one-dimensional elastic model. On the aforementioned assumption, the elastic modulus is determined to be the inverse number of the strain. Strictly, the aforementioned method is not an elastic modulus reconstruction method. With the aforementioned method, only the inverse number of strain is obtained, and accordingly, only relative elastic property of the tissue can be obtained as with the strain distribution.

Second, a method is known wherein elasticity equation is reduced to that without the stress terms (on the assumption that the tissue exhibits isotropic elasticity, incompressibility, and plane strain). With the aforementioned method, the elasticity equation formed so as to represent the plane-stress state is reduced to that without the stress terms, and the tissue elastic modulus distribution is reconstructed based upon the strain distribution (all the components of the strain tensor including the shear strain components) using the reduced elasticity equation without the stress terms so as to satisfy the boundary conditions (applied-pressure distribution on the body surface, or the displacement distribution thereof). Note that the present method requires the region (reference region) where the elastic modulus has been obtained beforehand.

Third, a method is known wherein the elasticity differential equation is integrated (on the assumption that the tissue exhibits isotropic elasticity, incompressibility, and plane strain). With the aforementioned method, the elasticity equation formed so as to represent the plane-stress state is reduced to that without the stress terms, and the tissue elastic modulus distribution is reconstructed based upon the strain distribution (all the components of the strain tensor including the shear strain components) by consecutively integrating the reduced differential equation without the stress terms with regard to the elastic modulus with the elastic modulus near the body surface as the reference. Note that the present method requires the region (reference region) near the body surface where the elastic modulus distribution has been obtained beforehand. Furthermore, the aforementioned method has a problem that the error of calculation becomes greater the farther away from the body surface, due to accumulation of the error since integration is made with the elastic modulus near the body surface as the reference.

Fourth, a method using the perturbation method is known (on the assumption that the tissue exhibits isotropic elasticity, near-incompressibility, and plane strain). With the aforementioned method, the tissue elastic modulus distribution is reconstructed by solving the elasticity equation which has been formed so as to represent the plane-strain state, based upon the applied-pressure distribution on the body surface and the strain distribution thereof in the ultrasonic-beam direction (axial direction) using the perturbation method with the iterative method.

Figure 7:
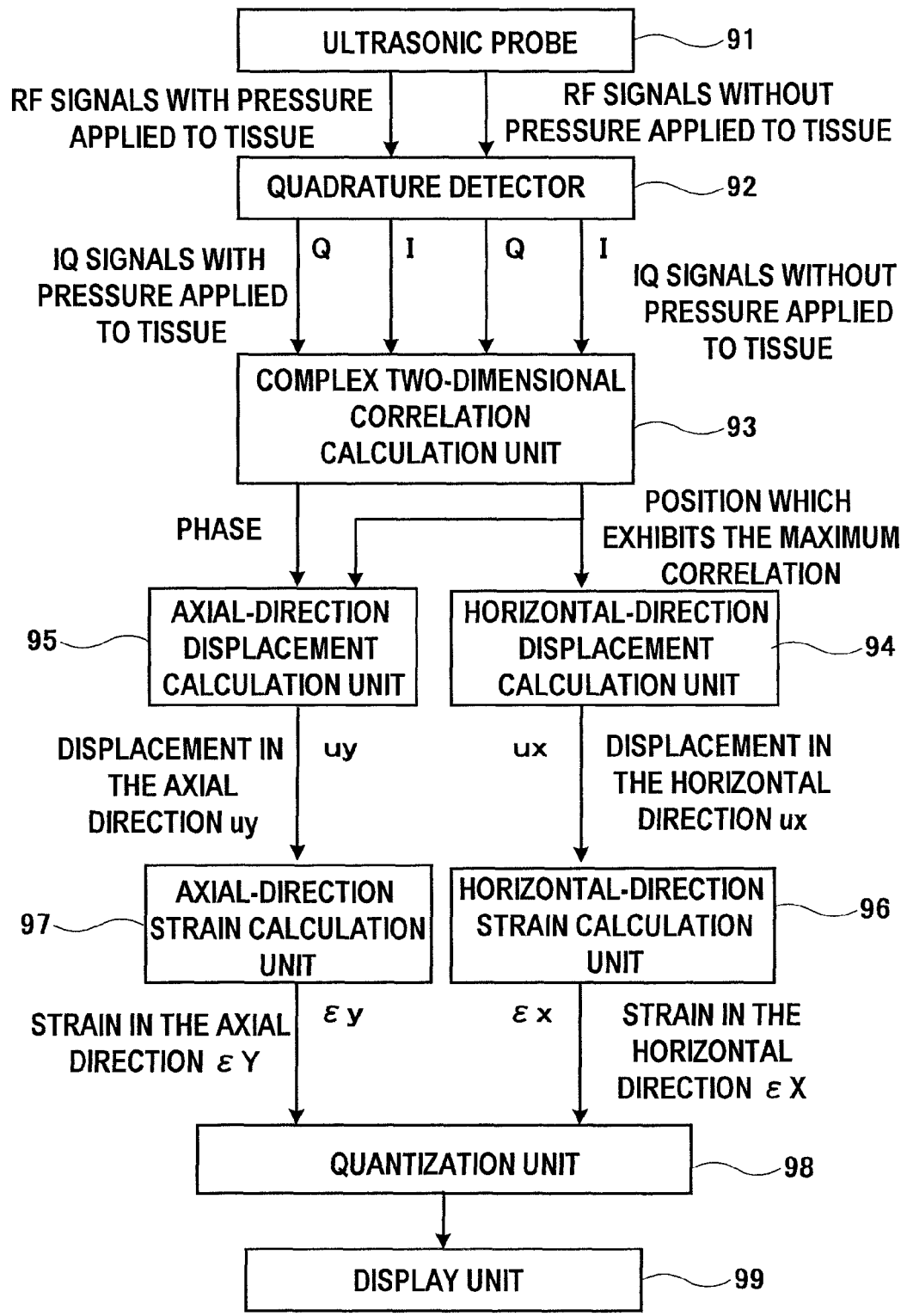
FIG. 7 is a block diagram which shows the schematic configuration of an ultrasonic diagnosis system according to an embodiment of the present invention.

Description has been made regarding the basic mechanism and the specific problems which are to be solved. Description will be made below regarding an embodiment according to the present invention, in order to solve the aforementioned problems. FIG. 7 is a block diagram which shows a schematic configuration of an ultrasonic diagnosis system according to an embodiment of the present invention. An ultrasonic probe 91 comprises a conventional sector scan probe (sector phased array probe), a linear scan probe (linear array probe), or a convex scan probe (convex array probe), having functions for casting an ultrasonic wave toward the tissue which is to be observed, and receiving the reflected ultrasonic wave.

The RF signals obtained with and without pressure applied to the tissue are output from the ultrasonic probe 91 to a quadrature detector 92. The quadrature detector 92 converts the RF signals with and without pressure applied to the tissue into the complex envelope signals (IQ signals) with and without application of pressure, and outputs the IQ signals to a complex two-dimensional correlation calculation unit 93. The complex two-dimensional correlation calculation unit 93 calculates two-dimensional correlation between the RF signals with and without pressure applied to the tissue, outputs the position which exhibits the maximum correlation to a horizontal-direction displacement calculation unit 94 and an axial-direction displacement calculation unit 95, and outputs the corresponding phase of the correlation function to an axial-direction calculation unit 95. Note that correlation is calculated in the axial direction at a pitch of a half the ultrasonic center frequency which is the maximum pitch for obtaining the phase while preventing aliasing. Correlation is calculated at such a pitch for enabling real-time display of the ultrasonic diagnosis system. Accordingly, the present invention is not restricted to calculation at a pitch of a half the wavelength, rather, an arrangement may be made wherein correlation is calculated with high precision.

The horizontal-direction displacement calculation unit 94 calculates the displacement $u_x$ in the horizontal direction based upon the position corresponding to the maximum correlation in the horizontal direction received from the complex two-dimensional correlation calculation unit 93, and outputs the displacement to a horizontal-direction strain calculation unit 96. On the other hand, the axial-direction displacement calculation unit 95 calculates the displacement $u_y$ in the axial direction based upon the position corresponding to the maximum correlation in the axial direction and the phase received from the complex two-dimensional correlation calculation unit 93, and outputs the displacement to an axial-direction strain calculation unit 97. The horizontal-direction strain calculation unit 96 makes spatial differentiation of the displacement u, in the horizontal direction received from the horizontal-direction calculation unit 94 so as to calculates the strain distribution $\epsilon_x$ in the horizontal direction, and outputs the strain distribution to a quantization unit 98. On the other hand, the axial-direction strain calculation unit 97 makes spatial differentiation of the displacement $u_y$ in the axial direction received from the axial-direction calculation unit 95 so as to calculate the strain distribution $\epsilon_y$ in the axial direction, and outputs the strain distribution to the quantization unit 98. The quantization unit 98 quantizes the strain distribution $\epsilon_x$ in the horizontal direction and the strain distribution $\epsilon_y$ in the axial direction in order to make grayscale display (or color display) thereof, and displays the information on a display unit 99. The display unit 99 displays each of the strain distributions thus quantized.

Next, description will be made regarding the operation of the expanded combined autocorrelation method employed in the ultrasonic diagnosis system shown in FIG. 7. First, let us consider a case wherein the tissue is compressed to a slight degree (i.e., several percent or less). In this case, from the local perspective, the pressure is assumed to cause parallel displacement for each point within the tissue. That is to say, the RF signals with and without pressure applied to the tissue are represented by the model represented by the following Expression.

$$i_1(t,x) = Re[A(t,x)e^{-j(\omega_0 t - \theta)}]$$

$$i_2(t,x) = Re[A(t-\tau, x-u_x)e^{-j[\omega_0(t-\tau)-\theta]}] \quad (13)$$

Here, $i_1(t, x)$ represents the RF signals without application of pressure, $i_2(t, x)$ represents the RF signals under pressure, $A(t, x)$ represents the envelope signals, $\omega_0$ represents the center angular frequency of the ultrasonic wave, $\tau$ represents the time shift serving as a time parameter which represents the displacement in the axial direction, $u_x$ represents the displacement in the horizontal direction, and $\theta$ represents the initial phase. Note that with the present method, the RF signals with and without application of pressure are represented by a model giving consideration to the displacement in the horizontal direction, unlike the Doppler method and the combined autocorrelation method. The parameter which is to be obtained in the final stage is the displacement $u_y = c\tau/2$ in the axial direction (i.e., the time shift $\tau$) and the displacement $u_x$ in the horizontal direction. Note that c represents the sound speed within the tissue, and is assumed to be constant within the tissue.

Then, the RF signals with and without pressure applied to the tissue are quadrature-detected by the quadrature detector 92. That is to say, the sine wave and the cosine wave having the same frequency as the center frequency of the ultrasonic wave are applied to the RF signals, following which low-pass filtering is further applied to the RF signals, whereby the complex base-band signals $s_1$ and $s_2$ are obtained as represented by the following Expression (14).

$$s_1(t,x) = A(t,x)e^{j\theta}$$

$$s_2(t,x) = A(t-\tau, x-u_x)e^{j(\omega_0 \tau + \theta)} \quad (14)$$

Then, the two-dimensional complex correlation function $R_{12}(t, x; n, m)$ between the $s_1(t, x)$ and $s_2(t+nT/2, x+mL)$ is defined as represented by the following Expression (15).

$$R_{12}(t, x; n, m) = \int_{-x_0/2}^{x_0/2} \int_{-t_0/2}^{t_0/2} s_1(t+v, x+w)s_2 \quad (15)$$
$$\left(t + n\frac{T}{2} + v, x + mL + w\right)^* dv dw$$
$$= R_A\left(t, x; t - n\frac{T}{2}, u_x - mL\right)e^{-j\omega_0(\tau - n\frac{T}{2})}$$

$(n = -N_{min}, \ldots, -2, -1, 0, 1, 2, \ldots, N_{max})$ $(m = -M_{min}, \ldots, -2, -1, 0, 1, 2, \ldots, M_{max})$ Here, T represents the cycle of the ultrasonic wave, L represents the sampling pitch (beam-line pitch), $R_A(t, x; \tau, u_x)$ represents the autocorrelation function of the envelope signals, t0 represents the length of the correlation window in the axial direction, x0 represents the length of the correlation window in the horizontal direction. On the other hand, v represents a variable value in the time (τ) axial direction for integration, and w represents a variable value in the beam-line direction for integration, and the asterisk "*" represents a complex conjugate operator. Then, the two-dimensional envelope correlation coefficient C(t, x; n, m) is defined using the two-dimensional complex correlation function as represented by the following Expression (16).

$$C(t, x; n, m) = \frac{|R_{12}(t, x; n, m)|}{\sqrt{|R_{11}(t, x; 0, 0)| \simeq |R_{22}(t, x; n, m)|}} \quad (16)$$

Note that $R_{11}(t, x; 0, 0)$ represents the autocorrelation function of $S_1(t, x)$, and $R_{22}(t, x; n, m)$ represents the autocorrelation function of $S_2(t+nT/2, x+mL)$. The envelope correlation coefficient is used for solving a problem of aliasing in the same way as with the combined autocorrelation method. That is to say, combinations {C(t, x; n, m), ϕ(t, x; n, m)} formed of C(t, x; n, m) and ϕ(t, x; n, m) of $R_{12}(t, x; n, m)$ are obtained for all the variable numbers n and m at each measurement point (t, x). With the present method, let us say that the variable number pair (n, m) is determined in a sufficient range, i.e., in a range sufficient for envelope correlation. In this case, the phase ϕ(t, x; k, l) corresponding to (n, m)=(k, l) which exhibits the maximum envelope correlation coefficient matches the phase without aliasing. The reason is that with the variable number pair (n, m) which exhibits the maximum envelope correlation coefficient as (k, l), the time shift |τ−kT/2| between $s_1(t, k)$ and $s_2(t+kT/2, x+lL)$ is smaller than T/2. That is to say, |ϕ(t, x; k, l)|=ω$_0$|t−kT/2| is smaller than π. That is to say, with the present method, calculation is made using ϕ(t, x; k, l) without aliasing, thereby obtaining the correct time shift τ, the correct displacement $u_y$ in the axial direction, and the correct displacement $u_x$ in the horizontal direction, at each measurement point (t, x) as represented by the following Expression (17).

$$\tau = -\frac{\phi(t, x; k, l)}{\omega_0} + k\frac{T}{2} \quad (17)$$
$$u_y = \frac{c\tau}{2}$$
$$u_x = lL$$

Note that c represents the sound speed within the tissue (which is assumed to be constant at 1500 m/s which is normal sound speed within soft tissue). With the present method, the calculation described above is made for all the measurement points, thereby obtaining the displacement distribution $u_y(x, y)$ in the axial direction and $u_x(x, y)$ in the horizontal direction.

Furthermore, with the present method, spatial differentiation is made for each of the aforementioned displacement distributions, whereby the strain distribution $\epsilon_y(x, y)$ in the axial direction and the strain distribution $\epsilon_x(x, y)$ in the horizontal direction are obtained as represented by the following Expression (18).

$$\epsilon_y(x, y) = \frac{\partial u_y(x, y)}{\partial y} \quad (18)$$

$$\epsilon_x(x, y) = \frac{\partial u_x(x, y)}{\partial x}$$

As described above, with the present method, the displacement (strain) distribution in the axial direction and in the horizontal direction is estimated based upon the RF signals with and without pressure applied to the tissue. Note that as can be understood from the above Expression $u_x$=lL, the precision of the displacement detection in the horizontal direction is limited by the sampling pitch (beam-line pitch) in the horizontal direction, and accordingly, the present method has the disadvantage of relatively low precision in the horizontal direction. However, the present method has the advantage of real-time observation, thereby improving practical performance.

The expanded combined autocorrelation method described above has a function for analyzing the relative displacement in the horizontal direction between the tissue and the ultrasonic probe under the pressure applied to the tissue using a two-dimensional correlation window applied in a predetermined range for each calculation, thereby handling displacement of the tissue in the horizontal direction. However, the present two-dimensional expanded combined autocorrelation method having such a function cannot estimate strain distribution containing displacement in the direction (direction orthogonal to the two-dimensional ultrasonic scanning plane (slice direction)) orthogonal to both the axial direction and the horizontal direction under the pressure applied to the tissue. In order to solve the aforementioned problem, the above two-dimensional expanded combined correlation method is easily expanded into the three-dimensional expanded combined autocorrelation method using a three-dimensional window applied to a three-dimensional range, thereby enabling the system to be more stable.

Figure 10:
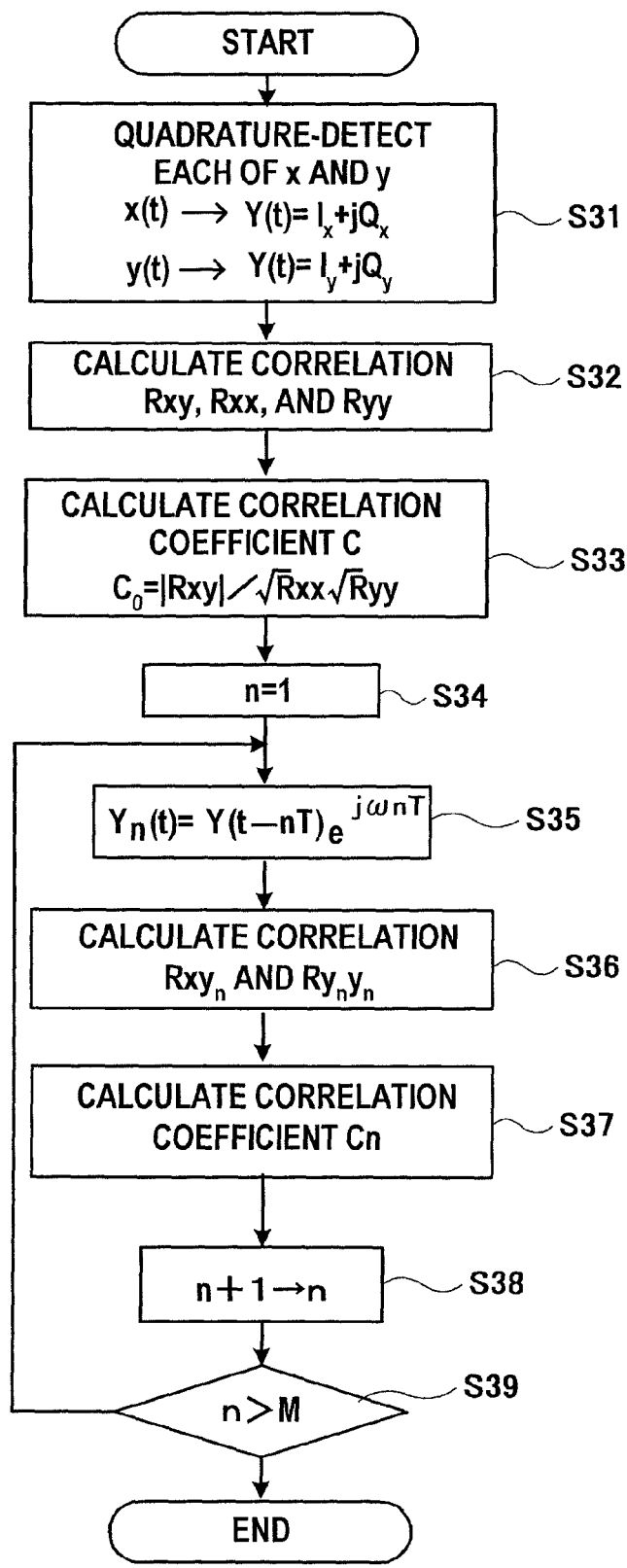
FIG. 10 is a flowchart for making detailed description regarding the combined autocorrelation method with improved calculation speed, which is performed in Step S15 shown in FIG. 9.

FIG. 9 and FIG. 10 are flowcharts for describing basic algorithm of the three-dimensional combined autocorrelation method. Note that FIG. 10 is a flowchart for making detailed description with regard to a part of the processing shown in FIG. 9.

In Step S11, a scanning-line resistor 1 stores "l", which serves as a counter for performing the same processing for the first scanning line through the L'th scanning line. The value stored in the scanning-line resistor l is checked in determination processing in Step S23.

In Step S12, the variable in the thickness direction (frame direction) is incremented in a range between −U and U for each loop processing. Note that the count is checked in the determination processing in Step S18.

In Step S13, the variable in the scanning direction (scanning line direction) is incremented in a range between −V and V for each loop processing. Note that the count is checked in the determination processing in Step S17.

In Step S14, the variable in the distance direction (axial direction) is incremented in a range between 0 and M for each loop processing. Note that the count is checked in the determination processing in Step S16.

In Step S15, correlation coefficient C(l, t; u, v, n) of the envelope signals in the distance direction (axial direction) is calculated with the combined autocorrelation method. Note that the conventional combined autocorrelation method cannot exhibit sufficient calculation speed for three-dimensional calculation, and accordingly, the correlation coefficient C(l, t; u, v, n) is calculated with the high-speed combined autocorrelation method. Description will be made later regarding the high-speed autocorrelation method.

In Step S16, processing is performed for the variable determined in the aforementioned Step S14. That is to say, determination is made whether or not the variable n stored in the distance-direction register has reached the predetermined maximum M. In the event that determination is made that the variable n has reached M, the flow proceeds to Step S17. Otherwise, the flow returns to Step S14, and the variable n stored in the distance-direction register is incremented.

In Step S17, processing is performed for the variable determined in the aforementioned Step S13. That is to say, determination is made whether or not the variable v stored in the scanning-direction register has reached the predetermined maximum V. In the event that determination is made that the variable v has reached V, the flow proceeds to Step S18. Otherwise, the flow returns to Step S13, and the variable v stored in the scanning-direction register is incremented.

In Step S18, processing is performed for the variable determined in the aforementioned Step S12. That is to say, determination is made whether or not the variable u stored in the thickness-direction register has reached the predetermined maximum U. In the event that determination is made that the variable u has reached U, the flow proceeds to Step S19. Otherwise, the flow returns to Step S12, and the variable u stored in the thickness-direction register is incremented.

In Step S19, the system searches the variable combination (u, v, n) in a range of u=(−U, . . . , 0, U), v=(−V, . . . , 0, . . . , V), and n=(0, 1, . . . , N) for the variable combination $(u_0, v_0, n_0)$ which exhibits the maximum correlation coefficient C(l, t; u, v, n) calculated in Step S12 through Step S18. Note that while the present embodiment employs such a distance-direction range n=(0, 1, . . . , N) under the assumption that only the positive pressure is applied to the tissue, it is needless to say that the distance-direction range n=(−M, . . . , 0, . . . , N) should be employed in an arrangement wherein both the positive and negative pressure is applied to the tissue.

In Step S20, the phase difference $\phi(l, t; u_0, v_0, n_0)$ of the correlation coefficient $C(l, t; u_0, v_0, n_0)$ obtained in Step S19 is calculated.

In Step S21, the phase difference $n_0\pi+\phi(l, t; u_0, v_0, n_0)$ is calculated as the phase difference in the final stage.

In Step S22, the displacement $v=v_0+\Delta v$ in the scanning direction, and $u=u_0+\Delta u$ in the thickness direction, are calculated using the correlation coefficient C(l, t; u, v, n) at a point (u, v, n) near the point $(u_0, v_0, n_0)$.

In Step S23, the variable stored in the scanning-line resistor 1 in the aforementioned Step S11 is checked. That is to say, determination is made whether or not the variable l has reached L. In the event that determination is made that l has reached L, the flow proceeds to Step S24. Otherwise, the flow returns to Step S11, and the variable stored in the scanning-line resistor 1 is incremented.

In Step S24, strain distribution is calculated by making spatial differentiation of the estimated displacement distribution under pressure applied to the tissue.

FIG. 10 is a flowchart for making detailed description regarding the aforementioned high-speed combined autocorrelation method in Step S15 shown in FIG. 9.

In Step S31, the RF signals x without application of pressure and the RF signals y under pressure are quadrature-detected, whereby I signals and Q signals are obtained as described below.

$x(t) \rightarrow Ix, Qx$ (where $X(t)=Ix+jQx$)

$y(t) \rightarrow Iy, Qy$ (where $Y(t)=Iy+jQy$)

In Step S32, the correlations Rxy, Rxx, and Ryy, are calculated based upon the following Expressions.

$Rxy=\int X(t+v)\cdot Y^*(t+v)dv$ $Rxx=\int X(t+v)\cdot X^*(t+v)dv$ $Ryy=\int Y(t+v)\cdot Y^*(t+v)dv$ In Step S33, the correlation coefficient $C_0$ is calculated based upon the correlations Rxy, Rxx, and Ryy, thus obtained, using the following Expression.

$C_0=|Rxy|/(\sqrt{Rxx \cdot Ryy})$

In Step S34, the variable number n is set to 1.
In Step S35, $Y_n(t)=Y(t-nT)e^{j\omega nT}$ is calculated.
In Step S36, $Rxy_n$ and $Ry_ny_n$ are calculated based upon the following Expressions.

$$Rxy_n = \int X(t+v) \cdot Y_n^*(t+v)dv$$
$$= \int X(t+v) \cdot Y^*(t-nT+v)e^{j\omega nT}dv$$
$$Ry_ny_n = \int Y_n(t+v) \cdot Y_n^*(t+v)dv$$
$$= \int Y(t-nT+v) \cdot Y^*(t-nT+v)dv$$

In Step S37, the correlation coefficient $C_n$ is calculated based upon the $Rxy_n$ and $Ry_ny_n$ thus obtained, using the following Expression.

$C_n=|Rxy_n|/(\sqrt{Rxx} \cdot \sqrt{Ry_ny_n})$

In Step S38, the variable number n is incremented.
In step S39, determination is made whether or not the variable number n has reached the predetermined maximum number M. In the event that determination is made that n has reached M, the processing ends. Otherwise, the flow returns to Step S35, and the same processing is repeated.

With the method shown in the flowchart in FIG. 10, $Y_n$ is calculated from Y in Step S35 in order to calculate $Rxy_n$ and $Ry_ny_n$. This enables a simple circuit configuration. Description will be made below regarding a method for calculating $Y_n$ from Y.

First, the echo signals x(t) without application of pressure are represented by the following Expression.

$x(t)=u(t)\cos(\omega t+\theta)$

On the other hand, the echo signals y(t) under pressure applied in the axial direction are represented by the following Expression.

$y(t)=x(t+\tau)=u(t+\tau)\cos(\omega(t+\tau)+\theta)$.

Then, the quadrature-detected signals of x, y, and $y_n$, are represented by the following Expressions.

$$x(t) \rightarrow$$
$$Ix = 0.5u(t)\cos\theta$$
$$Qx = -0.5u(t)\sin\theta$$
$$(X(t) = Ix + jQx = 0.5u(t)e^{-j\theta})$$
$$y(t) \rightarrow$$
$$Iy = 0.5u(t+\tau)\cos(\omega\tau + \theta)$$
$$Qy = -0.5u(t+\tau)\sin(\omega\tau + \theta)$$
$$(Y(t) = Iy + jQy = 0.5u(t+\tau)e^{-j(\omega\tau+\theta)})$$

-continued $$y_n(t) = y(t - nT)$$
$$= u(t + \tau - nT)\cos(\omega(t + \tau - nT) + \theta)$$
$$= u(t + \tau - nT)\cos(\omega t + \omega(\tau - nT) + \theta)$$

Here, T represents the half cycle. Then, $Iy_n$ and $Qy_n$ are obtained as represented by the following Expressions.

$$Iy_n = 0.5u(t+\tau-nT)\cos(\omega(\tau-nT)+\theta)$$

$$Qy_n = -0.5u(t+\tau-nT)\sin(\omega(\tau-nT)+\theta)$$

$$(Y_n = Iy_n + jQy_n = 0.5u(t+\tau-nT)e^{-j(\omega(\tau-nT)+\theta)})$$

Accordingly, the following relation is obtained based upon the above Expressions.

$$Y_n(t) = Iy_n + jQy_n$$
$$= 0.5u(t + \tau - nT)e^{-j(\omega(\tau-nT)+\theta)}$$
$$= Y(t - nT)e^{j\omega nT}$$

As can be understood from the above Expression, $Y_n(t)$ is calculated from $Y(t)=Iy+jQy$.

Accordingly, $Rxy_n$ and $Ry_n y_n$ are calculated from X and Y as represented by the following Expressions.

$$Rxy_n = 4\int X(t+v) \cdot Y_n^*(t+v)dv$$
$$= 4\int X(t+v) \cdot Y^*(t-nT+v)e^{j\omega nT}dv$$

$$|Rxy_n| = Ru_n$$
$$= \int u(t+v)u(t+\tau-nT+v)dv$$
$$= 4\int |X(t+v) \cdot Y_n^*(t+v)|dv$$
$$= 4\int |X(t+v) \cdot Y^*(t-nT+v)e^{j\omega nT}|dv$$
$$= 4\int |X(t+v) \cdot Y^*(t-nT+v)|dv$$

$$Ry_n y_n = \int u(t+\tau-nT+v)u(t+\tau-nT+v)dv$$
$$= 4\int |Y_n(t+v) \cdot Y_n^*(t+v)|dv$$
$$= 4\int Y(t-nT+v) \cdot Y^*(t-nT+v)dv$$

Here, the asterisk "*" represents a complex conjugate operator.

Figure 11:
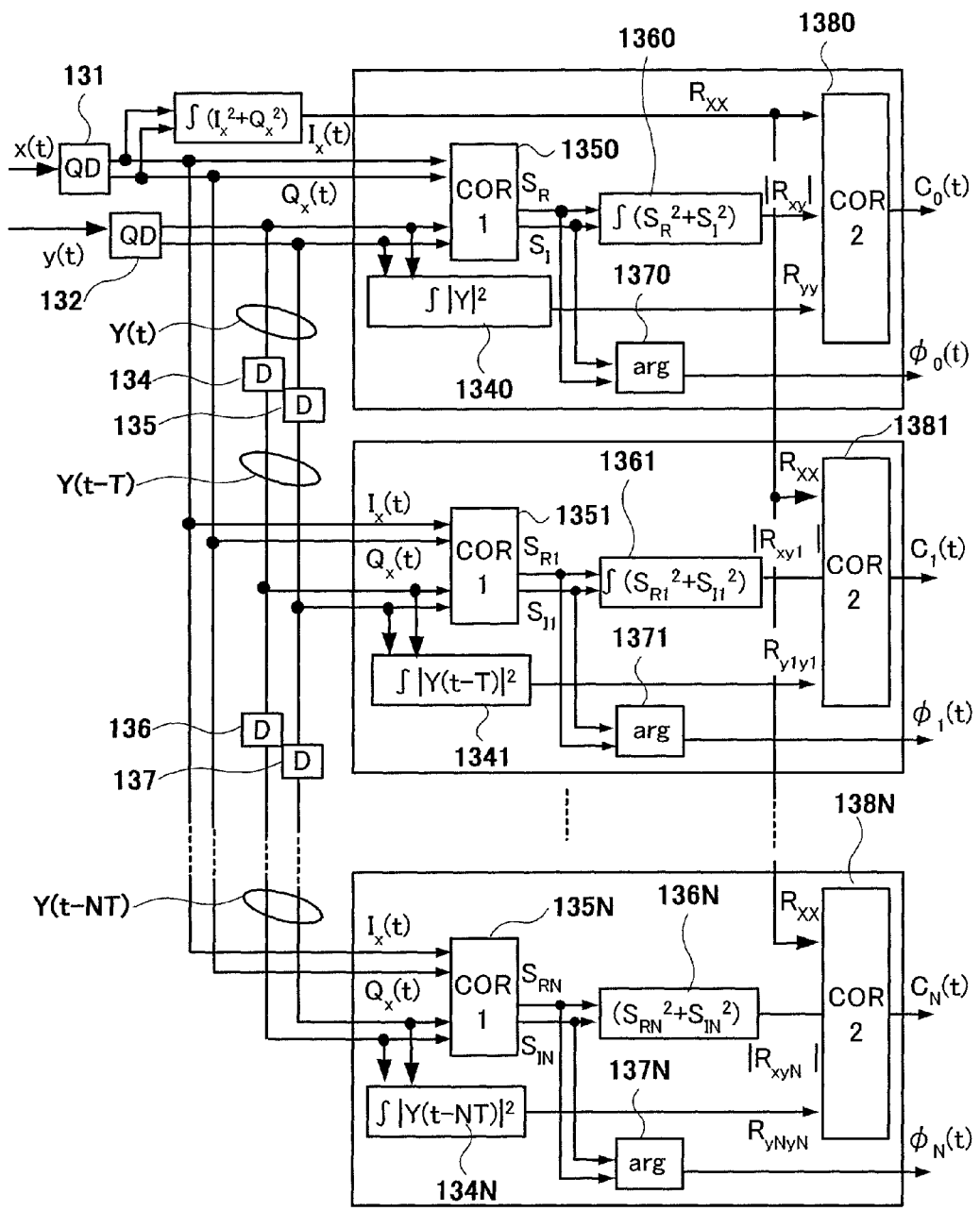
FIG. 11 is a block diagram which shows a circuit configuration for executing the basic algorithm of the three-dimensional combined autocorrelation method employed in the ultrasonic diagnosis system according to the present invention.

FIG. 11 is a block diagram which shows a circuit configuration for executing the basic algorithm of the three-dimensional combined autocorrelation method. With the conventional circuit configuration for executing the combined autocorrelation method as shown in FIG. 7, a great number of quadrature-detection circuits 1320 through 132N are arrayed, and processing in such a number of the quadrature-detection circuits 1320 through 132N requires enormous processing time, leading to difficulty in high-speed calculation, resulting in difficulty in real-time image display. Accordingly, the present embodiment employs the circuit configuration for executing the above-described basic algorithm as shown in FIG. 11, thereby enabling a high-speed circuit for executing the combined autocorrelation method.

The unpressed quadrature-detection circuit (QD) 131 receives the echo signals x(t) without application of pressure, quadrature-detects the received echo signals, and outputs the quadrature-detected signals Ix(t) and Qx(t) to the first correlation computing circuit 133 and the first correlation coefficient computing circuits 1350 through 135N. The pressed quadrature-detection circuit (QD) 132 receives the echo signals y(t) under pressure, quadrature-detects the received echo signals, and outputs the quadrature-detected signals Y(t)=Iy+jQy(Iy(t), Qy(t)) to the first correlation coefficient computing circuits 1350, the second correlation computing circuit 1340, the first delay circuit 134, and second delay circuit 135. The first delay circuit 134 and the second delay circuit 135 delay the quadrature-detected signals Y(t) by the cycle T of the ultrasonic wave, and output the delayed quadrature-detected signals Y(t−T) to the first correlation computing circuit 1351, the third delay circuit 136, and the fourth delay circuit 137. Each of the third delay circuit 136 and the fourth delay circuit 137 delay the quadrature-detected signals Y(t−T) by the cycle T of the ultrasonic wave, and output the delayed quadrature-detected signals Y(t−2T) to the subsequent first correlation coefficient computing circuit and delay circuit (not shown). In the same way, the quadrature-detected signals are consecutively delayed by the cycle T using each of the N delay circuit, and the delayed signals are output to the corresponding first correlation coefficient computing circuit.

The first correlation computing circuit 133 computes the correlation value Rxx based upon the signals Ix and Qx, and outputs the correlation value Rxx to the second correlation coefficient computing circuits 1380 through 138N. The second correlation computing circuit 1340 receives the quadrature-detected signals Iy(t) and Qy(t) from the pressed quadrature-detection circuit 132, computes the correlation value Ryy based upon the signals Iy and Qy, and outputs the correlation value Ryy to the second correlation coefficient computing circuit 1380. The first correlation coefficient computing circuit 1350 receives the quadrature-detected signals Ix(t) and Qx(t) from the unpressed quadrature-detection circuit 131, and the quadrature-detected signals Iy(t) and Qy(t) from the pressed quadrature-detection circuit 132, calculates the complex base-band signals $S_R$ and $S_I$, and outputs the complex base-band signals $S_R$ and $S_I$ to the third correlation computing circuit 1360 and the phase-difference computing circuit 1370. The third correlation computing circuit 1360 receives the complex base-band signals $S_R$ and $S_I$ from the first correlation coefficient computing circuit 1350, calculates the correlation value |Rxy| based thereupon, and outputs the correlation value |Rxy| to the second correlation coefficient computing circuit 1380. The phase-difference computing circuit 1370 receives the complex base-band signals $S_R$ and $S_I$ from the first correlation coefficient computing circuit 1350, and calculates the phase difference $\phi_0(t)$ based thereupon. The second correlation computing circuit 1380 receives the correlation value Rxx from the first correlation computing circuit 133, the correlation value |Rxy| from the third correlation computing circuit 1360, and the correlation value Ryy from the second correlation circuit 1340, computes the correlation coefficient $C_0(t)$ based upon these correlation values, and outputs the correlation coefficient $C_0(t)$.

The second correlation computing circuit 1341 receives the delayed quadrature-detected signals Iy(t−T) and Qy(t−T) from the first delay circuit 134 and the second delay circuit 135, computes the correlation value $Ry_1y_1$ based upon the signals Iy(t−T) and Qy(t−T), and outputs the correlation value $Ry_1y_1$ to the second correlation coefficient computing circuit 1381. The first correlation coefficient computing circuit 1351 receives the quadrature-detected signals Ix(t) and Qx(t) from the unpressed quadrature-detection circuit 131, and the delayed quadrature-detected signals Iy(t−T), and Qy(t−T) from the first delay circuit 134 and the second delay circuit 135, obtains the complex base-band signals $S_{R1}$ and $S_{I1}$, and outputs the complex base-band signals $S_{R1}$ and $S_{I1}$ to the third correlation computing circuit 1361 and the phase-difference computing circuit 1371. The third correlation computing circuit 1361 receives the complex base-band signals $S_{R1}$ and $S_{I1}$ from the first correlation coefficient computing circuit 1351, obtains the correlation value $|Rxy_1|$ based thereupon, and outputs the correlation value $|Rxy_1|$ to the second correlation coefficient computing circuit 1381. The phase-difference computing circuit 1371 receives the complex base-band signals $S_{R1}$ and $S_{I1}$ from the first correlation coefficient computing circuit 1351, and obtains the phase difference $\phi_1(t)$ based thereupon. The second correlation coefficient computing circuit 1381 receives the correlation value Rxx from the first correlation computing circuit 133, the correlation value $|Rxy_1|$ from the third correlation computing circuit 1361, and the correlation value $Ry_1y_1$ from the second correlation computing circuit 1341, calculates the correlation coefficient $C_1(t)$ based these correlation values, and outputs the correlation coefficient $C_1(t)$.

In the same way, with the second correlation computing circuits 1342 through 134N, the first correlation coefficient computing circuits 1352 through 135N, the third correlation computing circuits 1362 through 136N, the phase-difference computing circuits 1372 through 137N, and the second correlation coefficient computing circuits 1382 through 138N, arrayed downstream from the third delay circuit 135 and the fourth delay circuit 136, the same processing as described above is performed for each of the consecutively delayed quadrature-detected signals Iy(t−2T), ..., Iy(t−NT), and Qy(t−2T), ..., Qy(t−NT), whereby the correlation coefficients $C_2(t)$ through $C_N(t)$, and the phase $\phi_2(t)$ through $\phi_N(t)$, are output.

Next, description will be made regarding the elastic-modulus distribution reconstructing method using the three-dimensional finite element method. In order to simplify the inverse problem for reconstructing the elastic modulus distribution, with the present embodiment, the tissue is represented by a model. This allows the user to perform the elastic-modulus distribution reconstructing method proposed in the present embodiment using the finite element method. Specifically, with the present embodiment, the tissue is represented by a model on the assumption described below.

First, the tissue is assumed to exhibit isotropic elasticity. On the other hand, the distribution of the tissue strain is estimated for the tissue under external static pressure. Note that the static pressure is applied to the tissue so as to cause slight compression thereof, thereby allowing the user to make calculation using the relation between the RF signals with and without pressure applied to the tissue. Accordingly, in this case, the relation between the stress and the strain exhibits linearity. That is to say, approximate calculation can be made on the assumption that the tissue is represented by an elastic model. Furthermore, in this case, the tissue is assumed to be isotropic, and accordingly, the tissue is assumed to exhibits isotropic elasticity.

Furthermore, the tissue is assumed to exhibit near-incompressibility. In general, it is known that the tissue exhibits compressibility near incompressibility (Poisson's ratio ν=0.5). With the present embodiment, calculation is made with a constant Poisson's ratio of 0.49 within the tissue. Note that with the present embodiment, calculation is not made on the assumption that the tissue exhibits the complete incompressibility. The reason is that if calculation is made on the assumption that the tissue exhibits the complete incompressibility, i.e., calculation is made with a constant Poisson's ratio of 0.5 within the tissue, the elastic equation becomes a special case, leading to a problem that calculation cannot be made using the finite element method proposed in the present embodiment. Furthermore, with the present embodiment, the Poisson's ratio is assumed to be constant within the tissue, and accordingly, only the Young's modulus should be estimated for the elastic-modulus distribution, thereby reducing the inverse problem. Note that in general, the Poisson's ratio exhibits a relatively small variation as compared with the Young's modulus. Accordingly, with the present embodiment, calculation is made with the constant Poisson's ratio of 0.49 within the tissue.

Next, the tissue is represented by a three-dimensional finite element model. With the reconstructing method for the elastic modulus distribution according to the present embodiment, calculation is made using the finite element method, and accordingly, the tissue is divided into a finite number of rectangular parallelepiped elements. Note that each element is assumed to exhibit the constant elastic modulus, the constant stress, and the constant strain, therewithin. In general, in order to understand the method for solving the inverse problem, it is important to understand the forward problem corresponding to the inverse problem. With the present embodiment, the inverse problem is that the elastic modulus distribution is estimated based upon the strain distribution and the boundary conditions. Accordingly, the forward problem corresponding to the aforementioned inverse problem is that the strain distribution is calculated based upon the elastic modulus distribution and the boundary conditions. With the present embodiment, the aforementioned problem is solved using the finite element method (FEM: Finite Element Method) which is a kind of known numerical analysis methods.

With the finite element method, the tissue serving as a continuum which is to be estimated is represented by a model formed of a finite number of elements, and simultaneous linear equations which represent the properties of each element are solved using numerical analysis. Note that description will be made later regarding specific calculation using the finite element method. In brief, with the finite element method, the strain (displacement) distribution and the stress distribution serving as the output values are obtained based upon the elastic-modulus distribution of the tissue and the boundary conditions serving as the input values.

With the present embodiment, approximate calculation is made on the assumption that the tissue exhibits isotropic elasticity, and accordingly, the elastic equations (equilibrium equation, relation between strain and displacement, relation between stress and strain) hold under the conditions within the tissue as represented by the following Expressions.

The equilibrium equation is represented by the following Expression (19).

$$\frac{\partial \sigma_{ij}}{\partial x_j} + f_i = 0 \ (i, j = 1, 2, 3) \tag{19}$$

Here, the reference numeral 1, 2, and 3, serving as i and j, represent x, y, z, respectively. On the other hand, the relation between strain and displacement is represented by the following Expression (20).

$$\varepsilon_{ij} = \frac{1}{2}\left(\frac{\partial u_i}{\partial x_j} + \frac{\partial u_j}{\partial x_i}\right) \quad (20)$$

The relation between stress and strain (generalized Hooke's law) is represented by the following Expression (21).

$$\sigma_{ij} = \frac{E}{1+\nu}\left(\varepsilon_{ij} + \frac{\nu}{1-2\nu}\delta_{ij}\varepsilon_{nn}\right) \quad (21)$$

The aforementioned elastic equations are represented using tensors. Accordingly, there are actually three equilibrium equations, six strain-displacement relations, and six stress-strain relations. Note that the coordinate (x1, x2, x3) represents (x, y, z). Other reference characters represent the properties as follows.

E: Young's modulus (which is also referred to as "elastic modulus")
$\nu$: Poisson's ratio
$\epsilon_{ij}$: strain tensor
($\epsilon_{nn} = \epsilon_{11} + \epsilon_{22} + \epsilon_{33}$: strain of volume)
$s_{ij}$: stress tensor
$\delta_{ij}$: Kronecker delta
$u_i$: displacement vector
$f_i$: volume force vector
(Note that the gravity is deemed negligible, and accordingly, $f_i$ is assumed to be zero in this case)

The relation between the stress and the strain is then solved for $\epsilon_{ij}$. As a result, the relation between strain and stress is transformed as represented by the following Expression (22).

$$\varepsilon_{ij} = \frac{1+\nu}{E}\left(\sigma_{ij} - \frac{\nu}{1+\nu}\delta_{ij}\sigma_{nn}\right) \quad (22)$$

Here, $s_{nn} = s_{11} + s_{22} + s_{33}$. Then, i=j=2 is substituted into the above Expression (22), and the Expression is solved for the Young's modulus E, thereby obtaining the following Expression (23).

$$E = \frac{\sigma_{22} - \nu(\sigma_{11} + \sigma_{33})}{\varepsilon_{22}} \quad (23)$$
$$= \frac{\sigma_y - \nu(\sigma_x + \sigma_z)}{\varepsilon_y}$$

As can be understood from the above Expression (23), the Young's modulus, i.e., the elastic modulus can be calculated based upon the strain component in the axial direction (ultrasonic-wave beam direction, in the present embodiment), and the stress components in all directions. However, it is difficult to make direct measurement of the stress distribution used for the above Expression with the current techniques. Accordingly, with the present embodiment, the stress distribution and the elastic-modulus distribution are alternately estimated and updated such that the estimated elastic modulus distribution becomes close to the actual distribution. The specific procedure for reconstructing the elastic modulus distribution is performed as follows.

First, let us say that a uniform distribution is employed as the initial distribution $\{E^{^0}\}$ for estimating the elastic modulus distribution. Second, the stress distribution $\{S^{^0}\}$ caused due to the initial elastic modulus distribution $\{E^{^0}\}$ is calculated using the three-dimensional finite element method. Specifically, the strain-displacement relation and the stress-strain relation are substituted into the above equilibrium equation, whereby a new equilibrium equation is formed as represented by the following Expression (24). The new equilibrium equation is applied to each element within the tissue model.

$$\frac{\partial}{\partial x_j}\left[\frac{E}{2(1+\nu)}\left(\frac{\partial u_i}{\partial x_j} + \frac{\partial u_j}{\partial x_i}\right) + \frac{E\nu}{(1+\nu)(1-2\nu)}\delta_{ij}\frac{\partial u_n}{\partial x_n}\right] + f_i = 0 \quad (24)$$

Here, $$\frac{\partial u_n}{\partial x_n} = \frac{\partial u_1}{\partial x_1} + \frac{\partial u_2}{\partial x_2} + \frac{\partial u_3}{\partial x_3} \quad (25)$$

Then, the simultaneous equations are solved for the displacements using the Gaussian elimination under the following boundary conditions, whereby the displacement distribution $\{u^{^0}\}$ corresponding to the elastic modulus distribution $\{E^{^0}\}$ is obtained.

$$u_i|_{y=bottom} = 0$$

$$\sigma_i|_{y=top} = p_i$$

$$\sigma_n|_{x,z=side} = 0 \quad (26)$$

In the above Expressions, $p_i$ represents the external pressure vector on the body surface, and $s_n$ represents the stress component orthogonal to the side face. The first Expression represents the boundary condition that the bottom is fixed, the second Expression represents the boundary condition that the stress distribution on the body surface matches the external pressure distribution, and the third Expression represents the boundary condition that each side face has a free end. Next, the displacement distribution $\{u^{^0}\}$ is substituted into the strain-displacement relation, whereby the strain distribution $\{\epsilon^{^0}\}$ corresponding to the elastic modulus distribution $\{E^{^0}\}$ is obtained. Then, the strain distribution $\{\epsilon^{^0}\}$ is substituted into the stress-strain relation, whereby the stress distribution $\{S^{^0}\}$ corresponding to the elastic modulus distribution $\{E^{^0}\}$ is obtained.

Third, the elastic modulus distribution $\{E^{^k}\}$ is updated based upon the stress distribution calculated with the three-dimensional finite element method and the strain distribution ($\epsilon_y$) in the axial direction (y direction) estimated with the expanded combined autocorrelation method, using the following Expression (27).

$$\hat{E}^{k+1} = \frac{\hat{\sigma}_y^k - \nu(\hat{\sigma}_x^k + \hat{\sigma}_z^k)}{\varepsilon_y} \quad (27)$$

Note that the above Expression is obtained by solving the aforementioned stress-strain relation for the Young's modulus E with i=j=2. In the above Expression, k represents the iteration number.

Fourth, the three-dimensional finite element analysis is consecutively made based upon the elastic modulus distribution thus updated and the aforementioned boundary conditions, whereby the stress distribution is updated.

Then, the third and fourth processing are consecutively performed, whereby the elastic modulus distribution nears the actual elastic modulus distribution. Note that in the event that the elastic modulus distribution satisfies the following Expression (28), determination is made that convergence of the estimated elastic modulus distribution is achieved, and estimation processing ends.

$$\frac{1}{N}\sum_{l}^{N}|\hat{E}_{l}^{k+1} - \hat{E}_{l}^{k}| < \Gamma \qquad (28)$$

Here, l represents the element number, N represents the total number of the elements, and $\Gamma$ represents the threshold value.

Description has been made regarding the elastic modulus distribution reconstructing method using the three-dimensional finite element model proposed in the present embodiment. With the present method, the elastic modulus distribution is estimated based upon the three-dimensional equilibrium equation. Accordingly, with the present method, calculation is made with assumptions which are closer to actual tissue than with the conventional methods, thereby enabling more precise estimation of the elastic modulus distribution. Furthermore, with the present method, the elastic modulus distribution is reconstructed based upon the strain distribution in the axial direction alone which can be estimated with high precision, thereby enabling reconstruction of the elastic modulus distribution in a sure manner. Note that with the present method, the three-dimensional distribution of the elastic modulus is estimated for the tissue, and accordingly, there is the need to employ a two-dimensional array ultrasonic probe, or there is the need to make mechanical scanning of a one-dimensional array ultrasonic probe in the slice direction, for making three-dimensional scanning of the tissue which is to be analyzed.

Description will be made regarding the advantage of the reconstructing method for the elastic modulus distribution based upon the expanded combined autocorrelation method and the three-dimensional finite element model according to the present embodiment, which has been confirmed using simulation. FIG. 12 is a schematic diagram which shows the procedure of the simulation.

First, a tissue model having an elastic modulus distribution used for an estimation test is created. Note that the tissue model contains scattering points which reflect ultrasonic echo signals therewithin. Second, external pressure is applied to the tissue model so as to cause compression thereof in computer simulation. Then, the displacement of each scattering point due to the compression is calculated using the finite element method or the like. Third, the RF signals with and without application of pressure are simulated based upon the scattering-point displacement distribution with and without pressure applied to the tissue model. Fourth, the expanded combined autocorrelation method is applied to the simulated RF signals with and without application of pressure, whereby the tissue strain distribution is estimated. Fifth, the tissue elastic modulus distribution is estimated based upon the strain distribution estimated with the expanded combined autocorrelation method and the boundary conditions (external pressure distribution and so forth) determined for simulating compression of the tissue model using the elastic modulus distribution reconstructing method with the three-dimensional finite element model.

While various elastic modulus distributions were used for the tissue models in this simulation, all cases of elastic modulus distribution used here were assumed to exhibit isotropic elasticity. Note that the elastic modulus used in this simulation generally matches that of the mammary tissue corresponding to principal use of the tissue elastic modulus distribution measurement system according to the present embodiment. On the other hand, each tissue model contains scattering points therewithin for simulating the reflected RF signals with and without pressure applied to the tissue. Specifically, each tissue model contains the scattering points with average density of 500 points/cm³. Furthermore, the positions of the scattering points without application of pressure are determined using normal pseudo-random numbers with an average of 1.0 and standard deviation of 0.3. Then, the positions of the scattering points under pressure are obtained by calculating the displacement of each scattering point without application of pressure based upon the results from the finite element analysis. Here, while the information with regard to the scattering points within the actual tissue is unknown, each parameter of the scattering point is determined such that the B-mode image created based upon the simulated RF signals is similar to the B-mode image of the actual tissue.

With the present embodiment, the simulated RF signals with and without pressure applied to the tissue are calculated for each tissue model by convolution of the scattering-point function with and without application of pressure and the point spread function of the ultrasonic system as represented by the following Expression (29).

$$i_1(x,y,z) = \iiint h(x-x',y-y',z-z')t_1(x',y',z')dx'dy'dz'$$

$$i_2(x,y,z) = \iiint h(x-x',y-y',z-z')t_2(x',y',z')dx'dy'dz' \qquad (29)$$

Here, $i_1(x, y, z)$ represents the RF signals without pressure applied to the tissue, $i_2(x, y, z)$ represents the RF signals under pressure applied to the tissue, $h(x, y, z)$ represents the point spread function (impulse response) of the ultrasonic system, $t_1(x, y, z)$ represents the scattering-point function without pressure applied to the tissue, and $t_2(x, y, z)$ represents the scattering-point function under pressure applied to the tissue. Note that the scattering-point function represents the scattering coefficient thus predetermined at each scattering point, and represents a scattering coefficient of zero at positions other than the scattering points. On the other hand, the scattering-point function $t_2(x, y, z)$ under pressure applied to the tissue is calculated from the scattering-point function $t_1(x, y, z)$ without pressure applied to the tissue based upon the displacement of each scattering point due to strain of the tissue model. Note that the displacement of each scattering point due to compression of tissue is calculated by making linear interpolation of the displacement vectors at the element nodes calculated with the finite element analysis.

With the simulation according to the present embodiment, let us say that a non-focused ultrasonic system without damping of the ultrasonic wave is employed. That is to say, the point spread function $h(x, y, z)$ is assumed to be constant for each point. Furthermore, let us say that the point spread function can be separated into functions for each direction as represented by the following Expression (30).

$$h(x,y,z) = h_x(x)h_y(y)h_z(z) \qquad (30)$$

Figure 13A:
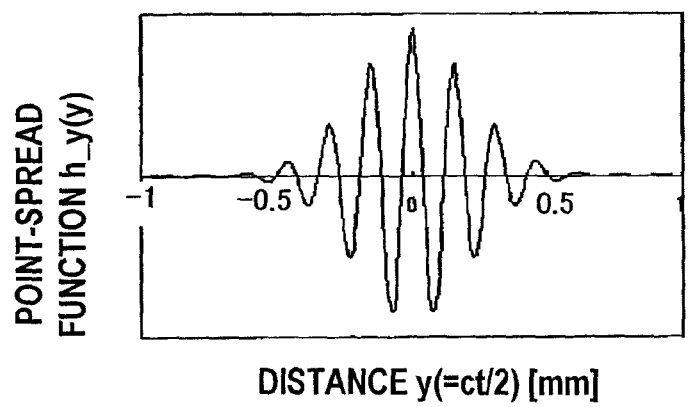
FIG. 13 is a diagram which shows an example of a point spread function for each point with the ultrasonic center frequency of 5.0 MHz.
Figure 13B:
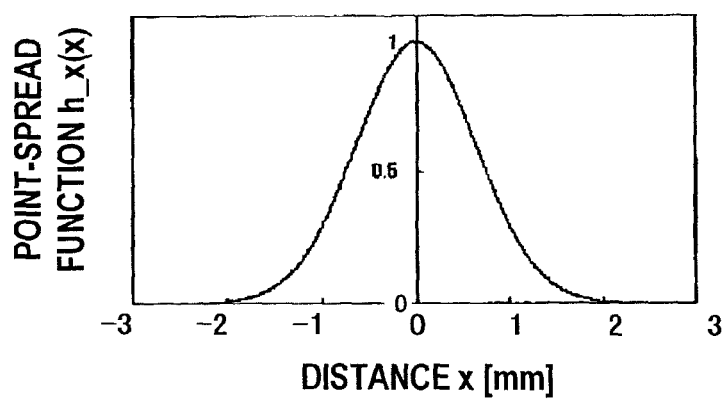
Figure 13C:
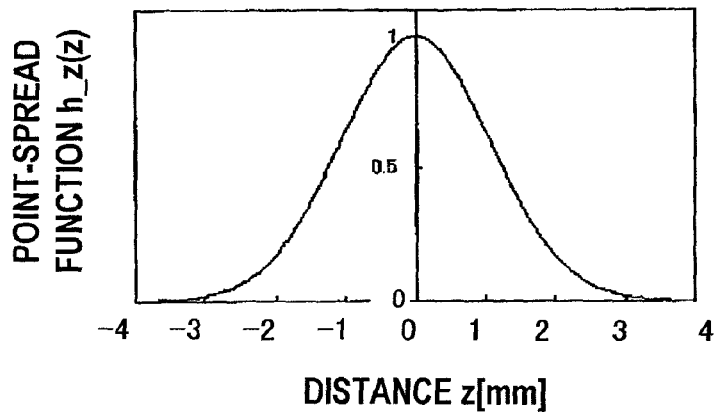

Here, $h_y(y)$ represents the point spread function in the direction of the ultrasonic beam. On the other hand, each of $h_x(x)$ and $h_z(z)$ represent the point spread function in the direction orthogonal to the ultrasonic-beam direction. Specifically, let us say that the x direction represents the in-plane direction (horizontal direction) of an ultrasonic tomographic image, and z direction represents the direction (slice direction) perpendicular to the ultrasonic tomographic image. Note that the point spread function in each direction is created based upon the reflected echo distribution obtained from actual measurement of the echo signals reflected from a wire target (a wire with a diameter of 0.13 mm extending in water) using an ultrasonic apparatus. FIG. 13 shows diagrams for describing each point spread function used for simulation with an ultrasonic center frequency of 5.0 MHz. FIG. 13(A) shows a point spread function $h_y(y)$ in the axial direction. The point spread function $h_y(y)$ is obtained by multiplying the Gaussian function by a sine wave, and serves as an approximate distribution of the actual reflected echo distribution reflected from the wire target. On the other hand, FIG. 13(B) shows the point spread function $h_x(x)$ in the horizontal direction, and FIG. 13(C) shows the point spread function $h_z(z)$ in the slice direction. Note that each of the aforementioned point spread functions are created using the Gaussian function so as to serve as an approximate distribution of the actual reflected echo distribution reflected from the wire target in the same way. The parameters of each function are varied corresponding to the center frequency, which will be described later in description of each simulation.

Next, description will be made regarding the advantage of the expanded combined autocorrelation method as a displacement (strain) distribution estimating method according to the present embodiment, which has confirmed by simulation. First, description will be made regarding the advantage of estimating the displacement of the tissue in the horizontal direction, which is the advantage to the combined autocorrelation method.

Figure 14:
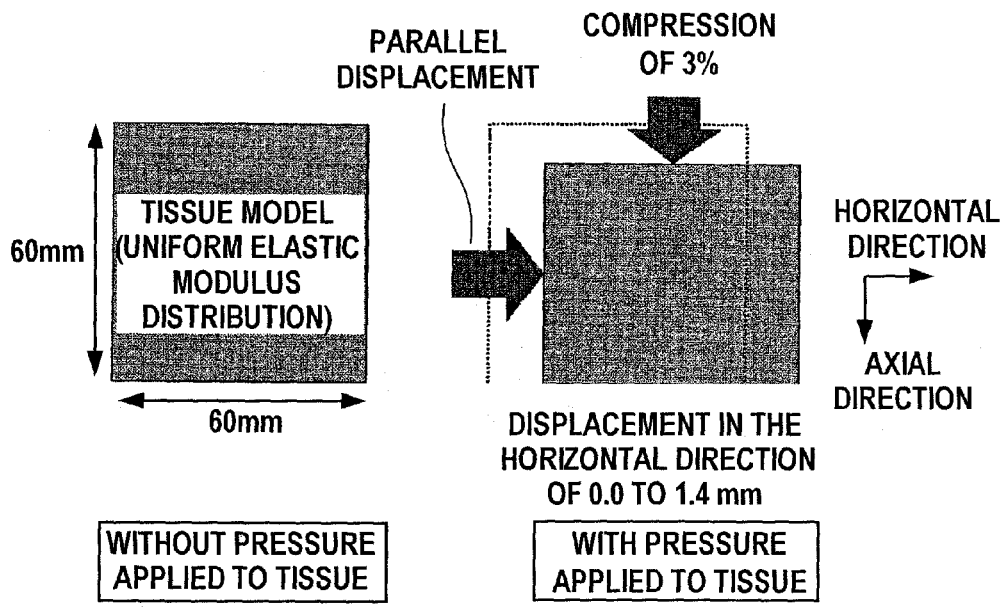
FIG. 14 is a schematic diagram which shows a tissue model.

FIG. 14 is a schematic diagram which shows a tissue model. The tissue model is formed with an outer size of 60 mm×60 mm (two-dimensional size), and with a uniform elastic modulus distribution. Then, compression of the tissue is simulated so as to cause uniform strain of 3% in the axial direction. Let us say that a simple one-dimensional elastic model is employed as the tissue model in this simulation for evaluating only the advantage of the expanded combined autocorrelation method. Furthermore, compression of the tissue in the axial direction is simulated with displacement of 0.0 mm to 1.4 mm in the horizontal direction for evaluating the advantage of handling displacement in the horizontal direction (relative displacement of the tissue in the horizontal direction as to the ultrasonic probe). Furthermore, let us say that simple parallel displacement of the tissue in the horizontal direction is simulated, which corresponds to a situation wherein the ultrasonic probe has slipped as to the tissue.

The RF signals are then simulated for the tissue model with and without strain of the tissue. The parameters used for simulation of the ultrasonic system include: a center frequency of 5.0 MHz, a pulse width of 0.5 mm; a ultrasonic beam width of 1.0 mm; a scanning line pitch of 0.5 mm; and a sampling frequency of 30 MHz. Then, the strain distribution is estimated based upon the simulated RF signals with and without application of pressure with the expanded combined autocorrelation method proposed in the present embodiment. In addition, the strain distribution estimated with the combined autocorrelation method and the strain distribution estimated with the spatial correlation method were prepared for comparison. Note that a correlation window with the same size was applied to each method with the same search range, thereby allowing the user to make simple comparison of precision and so forth therebetween. Specifically, the expanded combined autocorrelation method and the spatial correlation method employ a two-dimensional window with a size of 1.6 mm (axial direction)×2.5 mm (horizontal direction) for being applied in a two-dimensional search range of 5.6 mm (axial direction)×7.5 mm (horizontal direction). On the other hand, with the combined autocorrelation method for analyzing one-dimensional displacement, a one-dimensional correlation window with the same length of 1.6 mm in the axial direction was applied in the same range of 5.6 mm in the axial direction.

Figure 15:
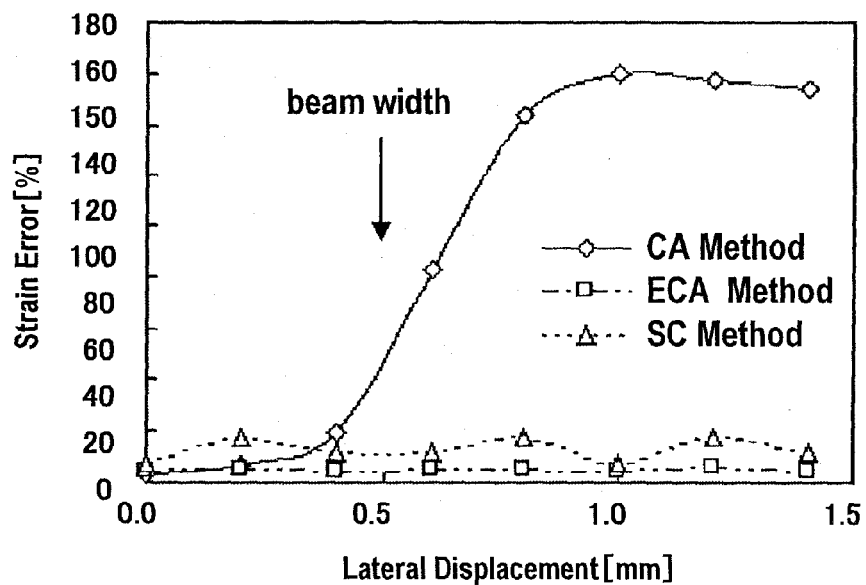
FIG. 15 is a diagram which shows the error of estimated strain with each estimating method due to displacement in the horizontal direction.
Figure 16A:
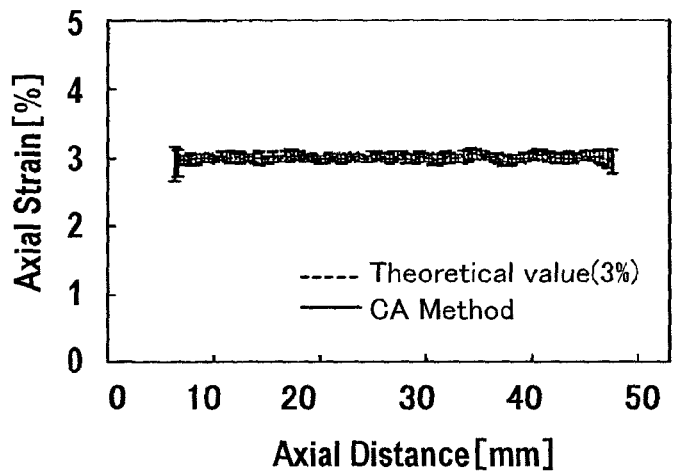
FIG. 16 is a diagram which shows the strain distribution estimated with each estimating method (combined autocorrelation method, expanded combined autocorrelation method, spatial correlation method) in a case of displacement of 0.0 mm in the horizontal direction.
Figure 16B:
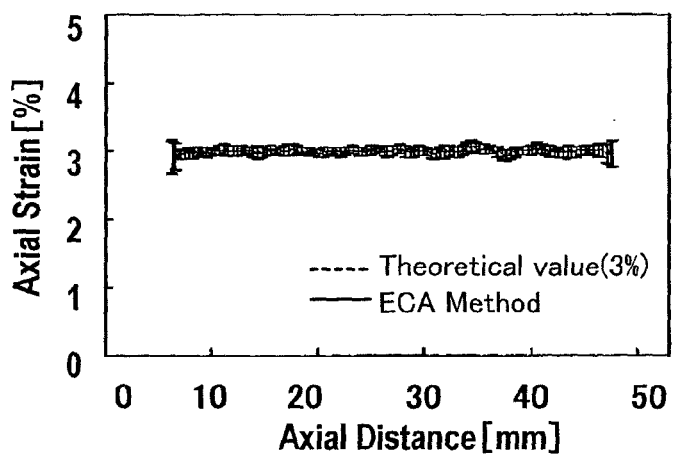
Figure 16C:
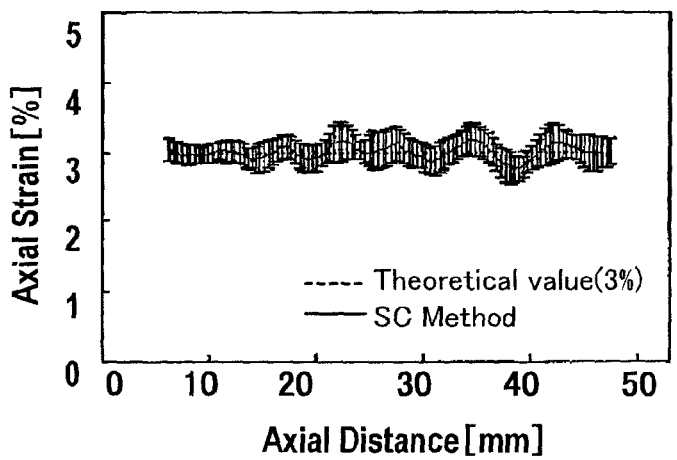
Figure 17A:
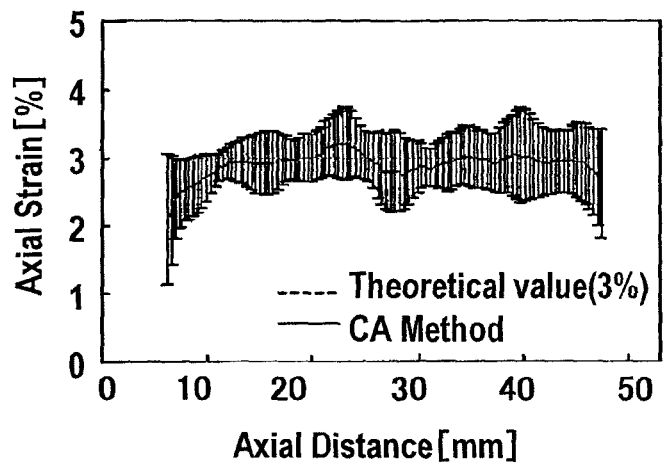
FIG. 17 is a diagram which shows the strain distribution estimated with each estimating method (combined autocorrelation method, expanded combined autocorrelation method, spatial correlation method) in a case of displacement of 0.4 mm in the horizontal direction.
Figure 17B:
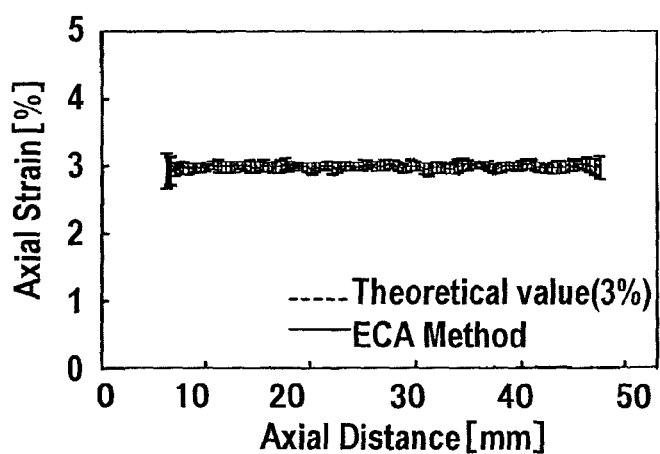
Figure 17C:
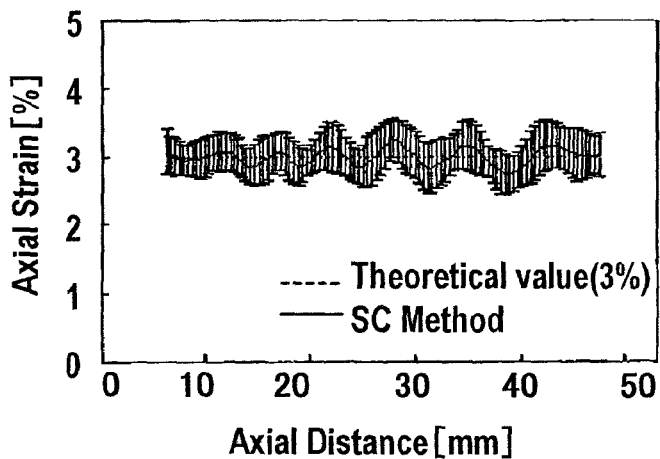
Figure 19A:
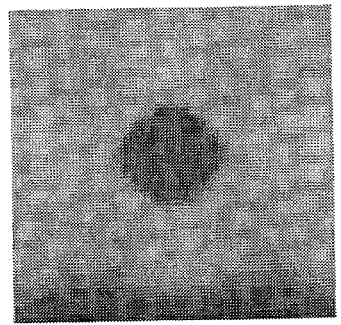
FIG. 19 shows estimated results of the strain distribution obtained from simulation of simple compression of the tissue model in the axial direction.
Figure 19B:
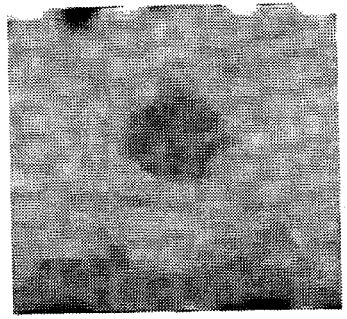
Figure 19C:
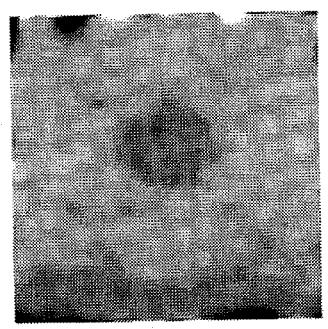
Figure 19D:
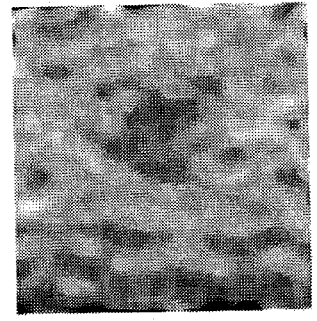
Figure 20A:
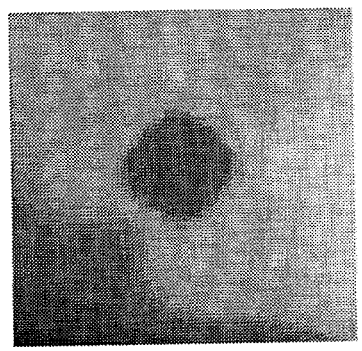
FIG. 20 shows estimated results of the strain distribution obtained from simulation of compression of the tissue model in a slant direction.
Figure 20B:
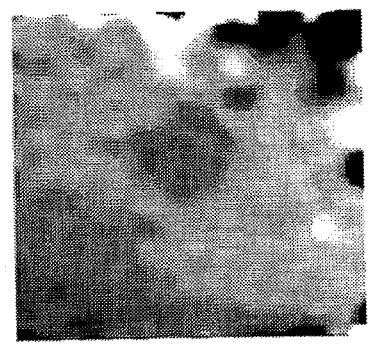
Figure 20C:
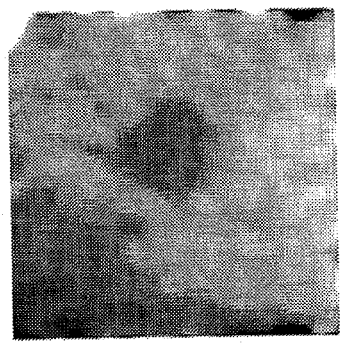
Figure 20D:
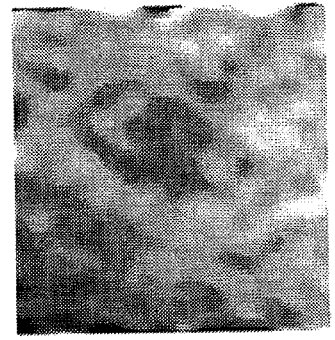

FIG. 15 through FIG. 17 show estimation results of the strain distribution with each method. FIG. 15 shows the error of the strain in the horizontal direction estimated with each method. Here, the reference symbol "◊" represents the error with the combined autocorrelation method, "□" represents the error with the expanded combined autocorrelation method, and "Δ" represents the error with the spatial correlation method. Note that the error of the estimated strain e is represented by the following Expression (31).

$$e = \sqrt{\frac{\sum_{i}^{N}(\hat{\varepsilon} - \varepsilon_i)^2}{\sum_{i}^{N}\varepsilon_i^2}} \tag{31}$$

Here, $e^{\hat{}}_i$ represents the estimated strain, $\epsilon_i$ represents the actual strain (ideal value), i represents the element number, and N represents the total number of the elements. On the other hand, FIG. 16 shows the estimated strain distributions of the tissue containing displacement in the horizontal direction of 0.0 mm, using each method (combined autocorrelation method, expanded combined autocorrelation method, and spatial correlation method). FIG. 17 shows the estimated strain distributions of the tissue containing displacement in the horizontal direction of 0.4 mm, using each method (combined autocorrelation method, expanded combined autocorrelation method, and spatial correlation method). Note that FIG. 16 and FIG. 17 show the average and the standard deviation of the estimated strain for each depth along the axial direction.

As can be understood from the simulation results, with the conventional combined autocorrelation method (CA method), relative displacement of the tissue in the horizontal direction exceeding the ultrasonic beam size (in this case, half the beam width, i.e., 0.5 mm) leads to rapid deterioration in estimation quality for the strain. On the other hand, it can be understood that the expanded combined autocorrelation method enables stable estimation of the strain regardless of the magnitude of the displacement in the horizontal direction. Furthermore, it can be understood that while the spatial correlation method enables stable estimation of the strain regardless of the magnitude of the displacement in the horizontal direction, as well, estimation results exhibit poor precision, i.e., exhibit twice or more the error as compared with the expanded combined autocorrelation method. Furthermore, making comparison between processing time of the aforementioned methods, while the expanded combined autocorrelation method requires processing time 3.6 times as great as with the combined autocorrelation method, the expanded combined autocorrelation method requires processing time only 1/(7.7) times as great as with the spatial correlation method, as shown in the following Table. As can be understood from the aforementioned results, the expanded combined autocorrelation method enables real-time calculation to a certain degree.

| Method | Processing time | Normalized processing time |
|---|---|---|
| Combined autocorrelation method | 26 seconds | 1/(3.6) |
| Expanded combined autocorrelation method | 1 minute 34 seconds | 1.0 |
| Spatial correlation method | 12 minutes 5 seconds | 7.7 |

Next, description will be made regarding estimation results with application of pressure in the slant direction. Note that with the present estimation, simulation is made using a tissue model having a three-dimensional structure as with the actual tissue, unlike the aforementioned simulation using a simple tissue model having a two-dimensional uniform structure. Note that pressure should be applied to the tissue with an ultrasonic probe in the ultrasonic-beam direction (axial direction) in ideal measurement. Now, description will be made regarding the estimation results affected by compression of the tissue in the slant direction.

FIG. 18 is a schematic diagram which shows a tissue model used for estimating the influence of compression of the tissue in a slant direction. As shown in FIG. 18(A), the tissue model has a three-dimensional structure with an outer size of 60 mm×60 mm×60 mm, and contains a cylindrical inclusion with a diameter of 15 mm and a length of 60 mm, and with high rigidity. Let us say that the material surrounding the inclusion has an elastic modulus (Young's modulus) of 10 Kpa, and the inclusion has the elastic modulus three times as great as that of the aforementioned material, i.e., have an elastic modulus (Young's modulus) of 30 Kpa. Note that the aforementioned elastic moduli are determined based upon the elastic moduli of the mammary tissue and the elastic modulus of the mammary cancer, of which diagnosis is the principal object of the present invention. Then, compression of the tissue model is simulated in the following two situations. The one situation corresponds to compression of the tissue model by 2% in the axial direction due to uniform external pressure of 200 Pa applied to the tissue model from the upper face along the axial direction as shown in FIG. 18(B). The other situation corresponds to compression of the tissue model in the slant direction due to uniform external pressure (200 Pa in the axial direction and 30 Pa in the horizontal direction) applied to the tissue model from the upper face along a slant direction as shown in FIG. 18(C).

Then, the RF signals with and without application of pressure are simulated for the aforementioned two situations, following which the strain distribution is estimated with the expanded combined autocorrelation method. Note that the strain distribution is estimated with the combined autocorrelation method and the spatial correlation method, as well, for comparison. Here, the correlation window having the same size is applied to calculation in the same search range for each method, thereby allowing simple comparison. Note that the correlation window has the same size as with the simulation described above. Furthermore, the other parameters for simulating the RF signals are determined to be the same values as with the above-described simulation. That is to say, the other parameters include: a center frequency of 5.0 MHz, a pulse width of 0.5 mm; a ultrasonic beam width in the horizontal direction of 1.0 a ultrasonic beam width in the slice direction of 2.0 mm; a scanning line pitch of 0.5 mm; and a sampling frequency of 30 MHz.

FIG. 19 and FIG. 20 show the simulation results in the aforementioned situations. FIG. 19 shows estimation results of the strain distribution in a simple situation wherein the tissue model is compressed in the axial direction. FIG. 20 shows estimation results of the strain distribution in a situation wherein the tissue model is compressed in a slant direction. Note that the strain distribution in the axial direction obtained by three-dimensional finite element analysis is employed as the strain distribution estimated with ideal method for each situation, which serves as the actual strain distribution. Note that FIG. 19 and FIG. 20 are cross-sectional views of the tissue model taken along the center line thereof, which show estimation results. In FIG. 20, the strain distribution estimated with an ideal method exhibits left-right asymmetry. The reason is that pressure is applied in a slant direction. Specifically, in this case, the pressure is applied in a lower-right direction in the drawing, leading to large displacement in the horizontal direction at the upper-right part in the drawing.

First, it has been confirmed that the expanded combined autocorrelation method exhibits generally the same estimation results for the strain distribution containing compression in the axial direction as with the combined autocorrelation method. On the other hand, in a situation wherein pressure is applied to the tissue in a slant direction, it has been also confirmed that while some regions cannot be estimated with the combined autocorrelation method due to great displacement in the horizontal direction, the expanded combined autocorrelation method enables stable estimation of the strain distribution regardless of the magnitude of the displacement in the horizontal direction as in the above description of the aforementioned simulation. On the other hand, it has been also confirmed that while the spatial correlation method enables stable estimation regardless of the magnitude of the displacement in the horizontal direction, the spatial correlation method has significantly poorer estimation precision as compared with the expanded autocorrelation method. In addition to the simulation results described above, it has been confirmed that the expanded combined autocorrelation method has the advantage of estimation of strain distribution.

As described above, it has been confirmed that the tissue-strain distribution can be estimated with high precision at high speed using the aforementioned expanded combined autocorrelation method. Now, description will be made regarding the estimation results obtained by simulation for the elastic modulus distribution reconstructing method with the three-dimensional finite element model proposed in the present embodiment. Note that the elastic modulus distribution reconstructing method is a method for estimating the elastic modulus distribution based upon the strain distribution, which serves as a method performed in the second stage in the tissue elasticity imaging system.

Figure 21A:
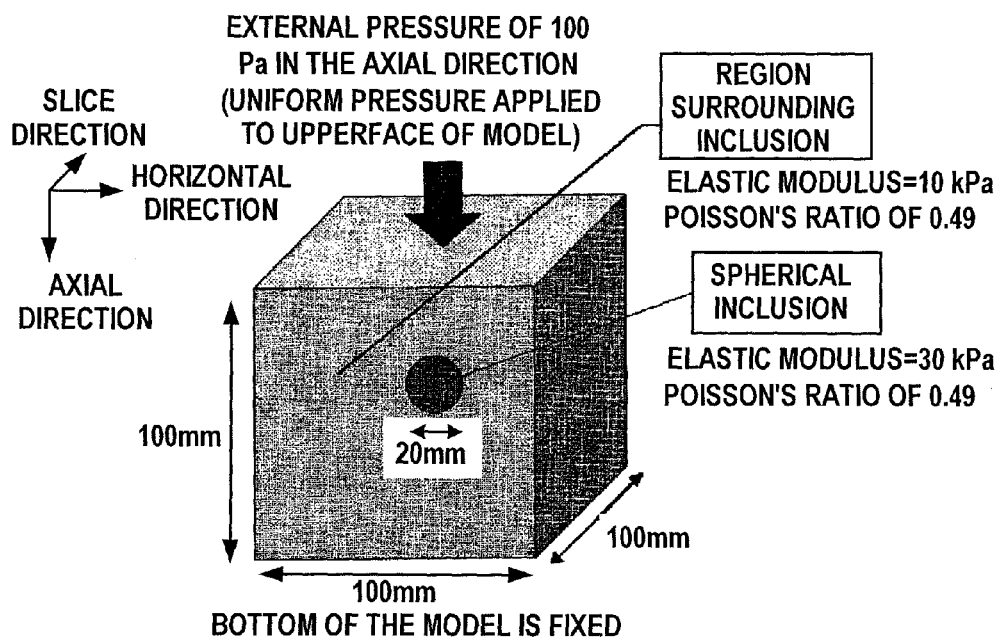
FIG. 21 is a diagram which shows two tissue model examples each of which have a three-dimensional structure.
Figure 21B:
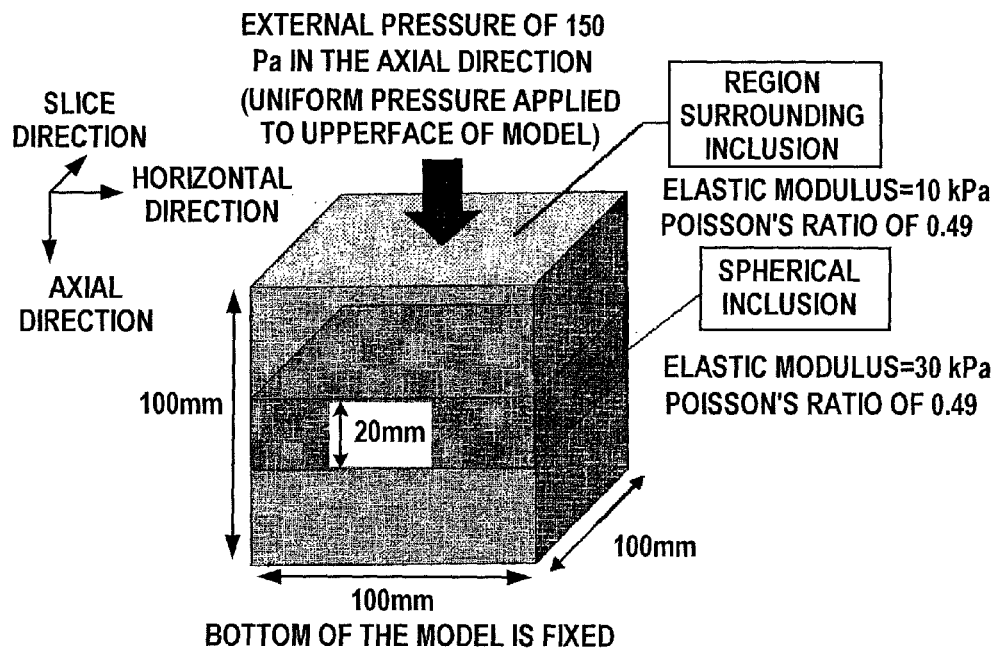
Figure 22A:
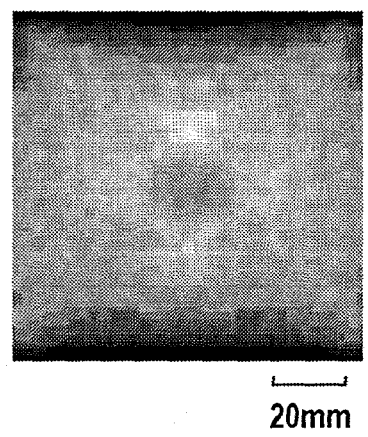
FIG. 22 is a first diagram which shows estimated results with an inclusion-containing model.
Figure 22B:
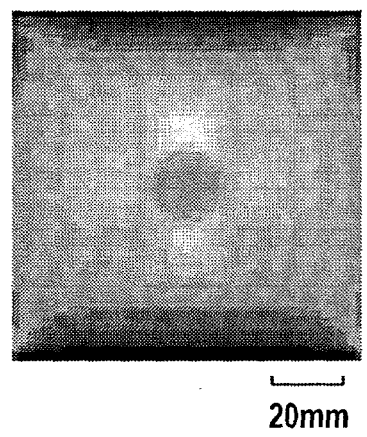
Figure 22C:
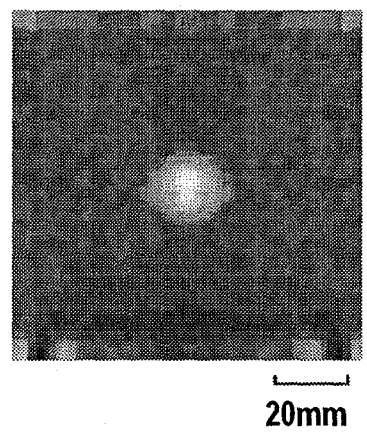
Figure 22D:
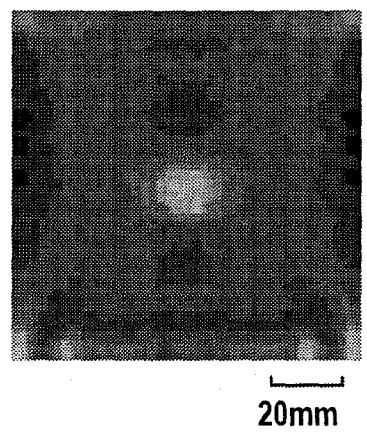

The elastic modulus distribution reconstructing method proposed in the present embodiment has the principal function for estimating the elastic modulus distribution based upon the three-dimensional kinetic equilibrium equation. Now, the advantages of the elastic modulus distribution reconstructing method proposed in the present embodiment are confirmed by making comparison between the elastic modulus distribution reconstructing method according to the present embodiment and the two-dimensional reconstructing method having the same processing except for calculation using the two-dimensional kinetic equilibrium equation. Note that calculation with the two-dimensional reconstructing method is made on the assumption that the plane strain occurs in the tissue. In the present simulation, two models each of which have a three-dimensional structure as with the actual tissue are employed as the tissue models as shown in FIG. 21. That is to say, FIG. 21 shows two tissue model examples each of which have a three-dimensional structure. FIG. 21(a) shows an inclusion-containing model containing an inclusion serving as a mammary tumor model. Specifically, the inclusion-containing model has an outer size of 100 mm×100 mm×100 mm, and contains a rigid inclusion with a diameter of 20 mm. Let us say that the inclusion has an elastic modulus of 30 kPa, and the material surrounding the inclusion has an elastic modulus of 10 kPa. The aforementioned elastic moduli are determined based upon the elastic modulus of the actual mammary tissue in the same way as with the simulation described above. On the other hand, both the inclusion and the material surrounding the inclusion exhibit near-incompressibility, and accordingly, both are assumed to have the same Poisson's ratio of 0.49. FIG. 21(b) shows a layer-structure model for simulating a layer-structure tissue such as a muscle. The layer-structure model has an outer size of 100 mm×100 mm×100 mm, and contains a rigid layer with a thickness of 20 mm. Let us say that the rigid layer has an elastic modulus of 30 kPa, and the material surrounding the rigid layer has an elastic modulus of 10 kPa. Note that the layer-structure model has a uniform Poisson's ratio of 0.49, as well.

Then, in a case of the inclusion-containing model shown in FIG. 21(a), compression under uniform external pressure of 100 Pa from the upper face of the model along the axial direction is simulated on a computer. On the other hand, in a case of the layer-structure model shown in FIG. 21(b), compression under uniform external pressure of 150 Pa from the upper face of the model along the axial direction is simulated on a computer. Note that compression under different external pressure is simulated for the aforementioned two models such that the same strain of approximately 1% is simulated for each model. Then, the RF signals with and without application of pressure are simulated for each tissue model, and the strain distribution in the axial direction is estimated with the expanded combined autocorrelation method. Subsequently, the elastic modulus distribution is estimated based upon the estimated strain distribution in the axial direction and the boundary conditions determined for the simulation of compression, using the three-dimensional elastic modulus distribution reconstructing method. Also, the elastic modulus distribution is estimated based upon the same strain distribution in the axial direction and the same boundary conditions using the two-dimensional reconstructing method for comparison. Here, the parameters used for simulating the RF signals include: a center frequency of 3.75 MHz, a pulse width of 0.75 mm; a ultrasonic beam width in the horizontal direction of 2.0 mm; a ultrasonic beam width in the slice direction of 2.0 mm; and a scanning line pitch of 2.0 mm. On the other hand, the parameters used for calculation with the expanded combined autocorrelation method include the size of the correlation window of 3.2 mm (in the axial direction)×4.0 mm (in the horizontal direction), and the search range of 11.2 mm (in the axial direction)×14.0 mm (in the horizontal direction). On the other hand, with the elastic modulus distribution reconstructing method using the three-dimensional finite element model, each tissue model is formed of 50,000 rectangular-parallelepiped elements each of which have a size of 2 mm (in the axial direction)×2 mm (in the horizontal direction)×5 mm (in the slice direction).

Figure 23A:
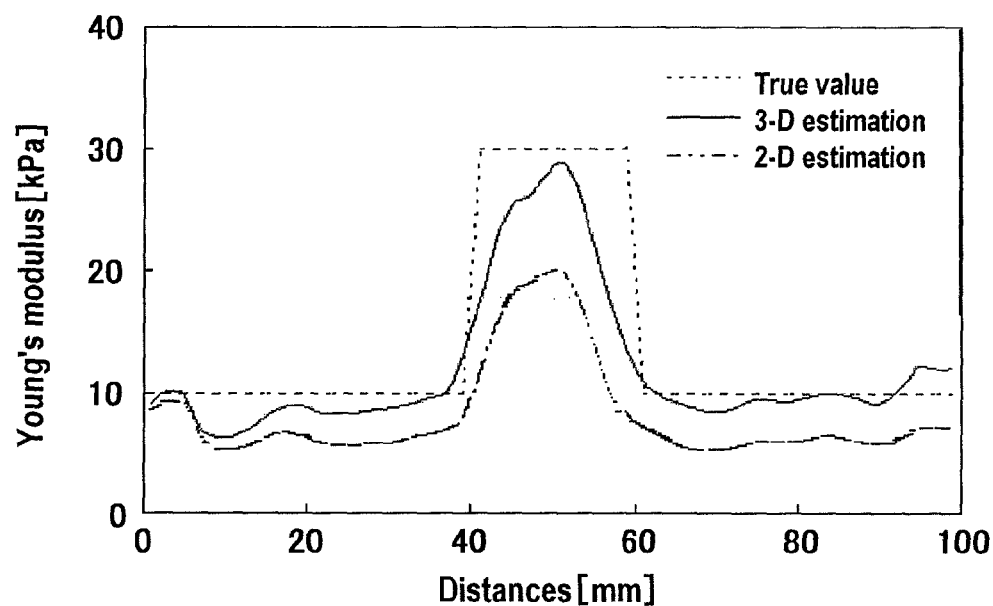
FIG. 23 is a second diagram which shows estimated results with the inclusion-containing model.
Figure 23B:
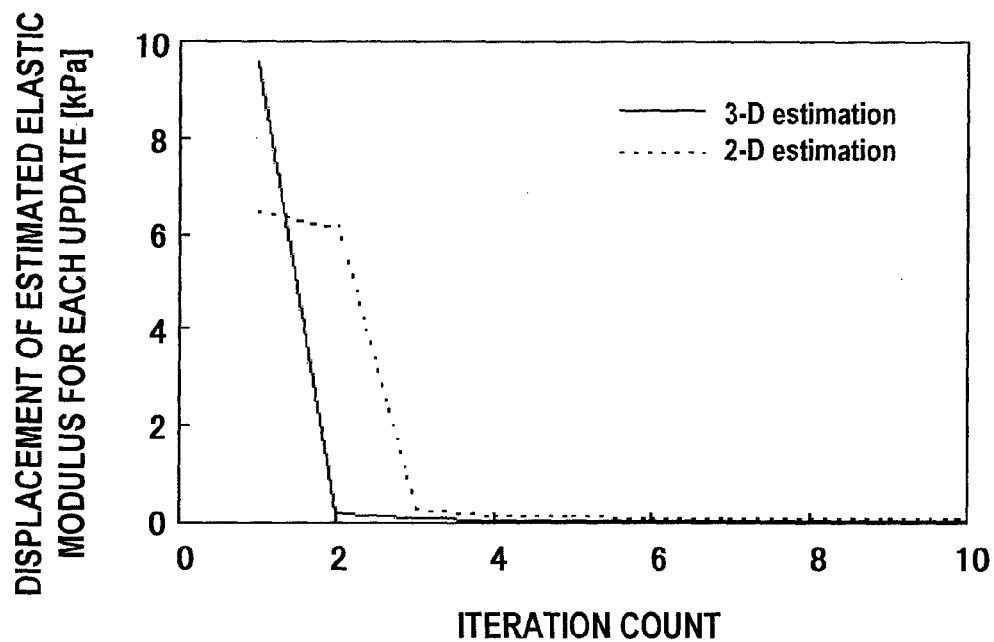
Figure 24A:
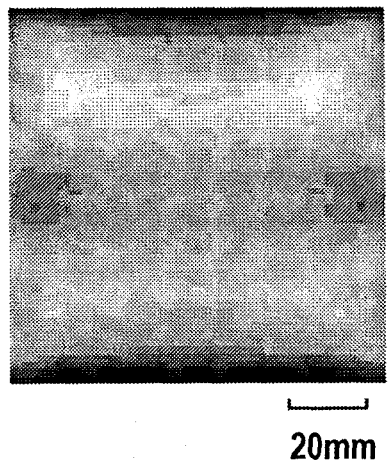
FIG. 24 is a first diagram which shows estimated results with a layer-structure model.
Figure 24B:
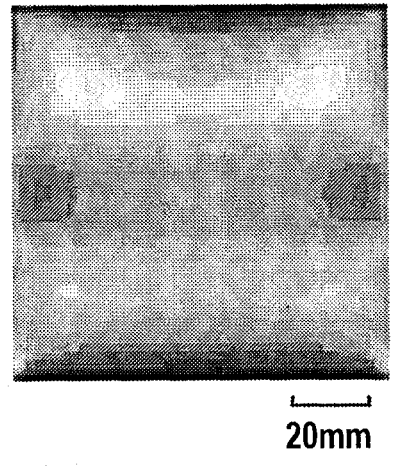
Figure 24C:
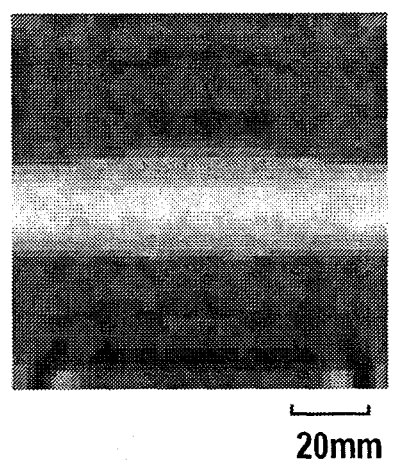
Figure 24D:
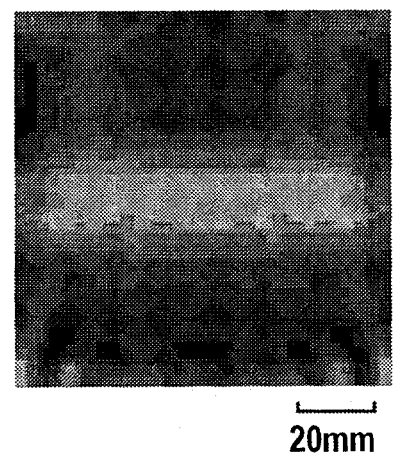
Figure 25A:
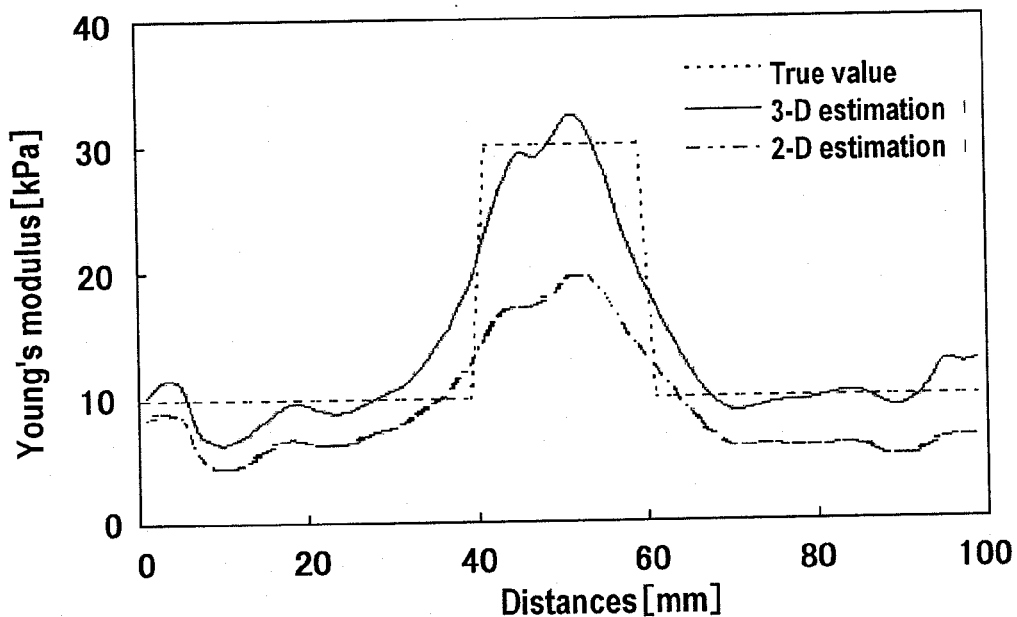
FIG. 25 is a second diagram which shows estimated results with the layer-structure model.
Figure 25B:
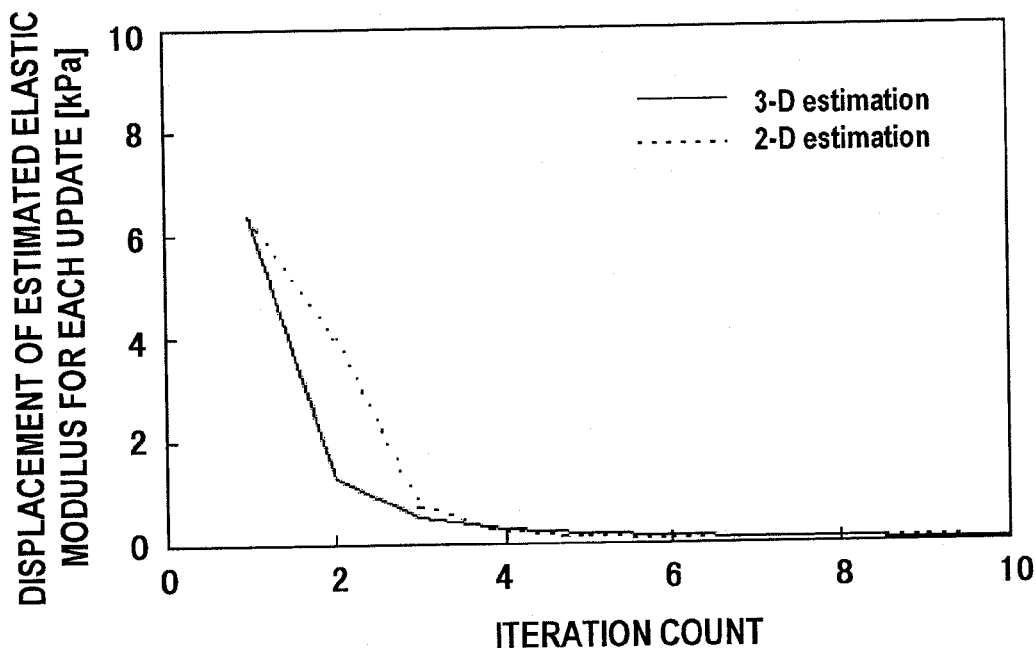

FIG. 22 through FIG. 25 show the simulation results. FIG. 22 and FIG. 23 show the estimation results for the inclusion-containing model. On the other hand, FIG. 24 and FIG. 25 show the estimation results for the layer-structure model. Note that while the three-dimensional distribution of the elastic modulus can be estimated with the three-dimensional reconstructing method, each of FIG. 24 and FIG. 25 show a cross-sectional view thereof taken along the center line of the model. The reason is that only the two-dimensional elastic modulus distribution can be estimated with the two-dimensional reconstructing method. Accordingly, FIG. 24 and FIG. 25 show a cross-sectional view of the estimation results taken along the center line of the model, thereby allowing the user to make comparison therebetween. On the other hand, estimation values for the three-dimensional reconstructing method and the two-dimensional reconstructing method obtained using each tissue model are listed in the following Table.

| | | Error of elastic modulus in region surrounding core of model [%] | Standard deviation in region surrounding core of model [%] | Error of contrast in core of model [%] |
|---|---|---|---|---|
| Inclusion-containing model | Three-dimensional reconstructing method | 3.5 | 15.5 | 11.0 |
| | Two-dimensional reconstructing method | 30.9 | 17.9 | 35.9 |
| Layer-structure model | Three-dimensional reconstructing method | 8.5 | 26.8 | 3.1 |
| | Two-dimensional reconstructing method | 24.9 | 22.1 | 43.5 |

The estimation parameters used here include: the error of elastic modulus $e_S$ in the region surrounding the core of the model; the standard deviation $SD_S$ in the region surrounding the core of the model; and the error of the contrast $e_C$ in the core region of the model, which are defined by the following Expressions.

$$e_s = \frac{\frac{1}{N_s}\sum_i^{N_s}|\hat{E}_i - E_i|}{\bar{E}_s} \quad (32)$$

$$SD_s = \frac{\sqrt{\frac{1}{N_s}\sum_i^{N_s}(\hat{E}_i - \bar{E}_s)^2}}{\bar{E}_s}$$

$$e_c = \frac{|(\hat{E}_c - \bar{E}_s) - (E_c - E_s)|}{E_c - E_s}$$

Note that in the aforementioned Expressions, S represents the sum in the region surrounding the core, $\hat{E}$ represents the estimated elastic modulus, E represents the actual elastic modulus, $N_S$ represents the total number of the elements in the region surrounding the core, $\hat{E}_S$ represents the average of the elastic modulus in the region surrounding the core of the model, $\hat{E}_C$ represents the estimated elastic modulus in the core region of the model, $E_C$ represents the actual elastic modulus in the core region of the model, and $E_S$ represents the actual elastic modulus in the region surrounding the core of the model.

As can be understood from the aforementioned simulation results, it has been confirmed that the elastic modulus distribution reconstructing method with the three-dimensional finite element model proposed in the present embodiment has the advantage of estimating the elastic modulus distribution with higher precision than with the two-dimensional reconstructing method formed on the assumption that plane stress occurs within the tissue. While three-dimensional reconstructing method enables precise estimation of the elastic modulus distribution, the elastic modulus distribution estimated with the two-dimensional reconstructing method exhibits smaller values than those of the actual elastic modulus distribution. It is needless to say that the reason is that with the two-dimensional reconstructing method, calculation in the direction orthogonal to the two-dimensional calculation plane is limited. In the present evaluation, it has been clearly confirmed that the elastic modulus distribution reconstructing method with the three-dimensional calculation corresponding to the actual tissue is suitably employed for analyzing actual tissue.

Figure 26:
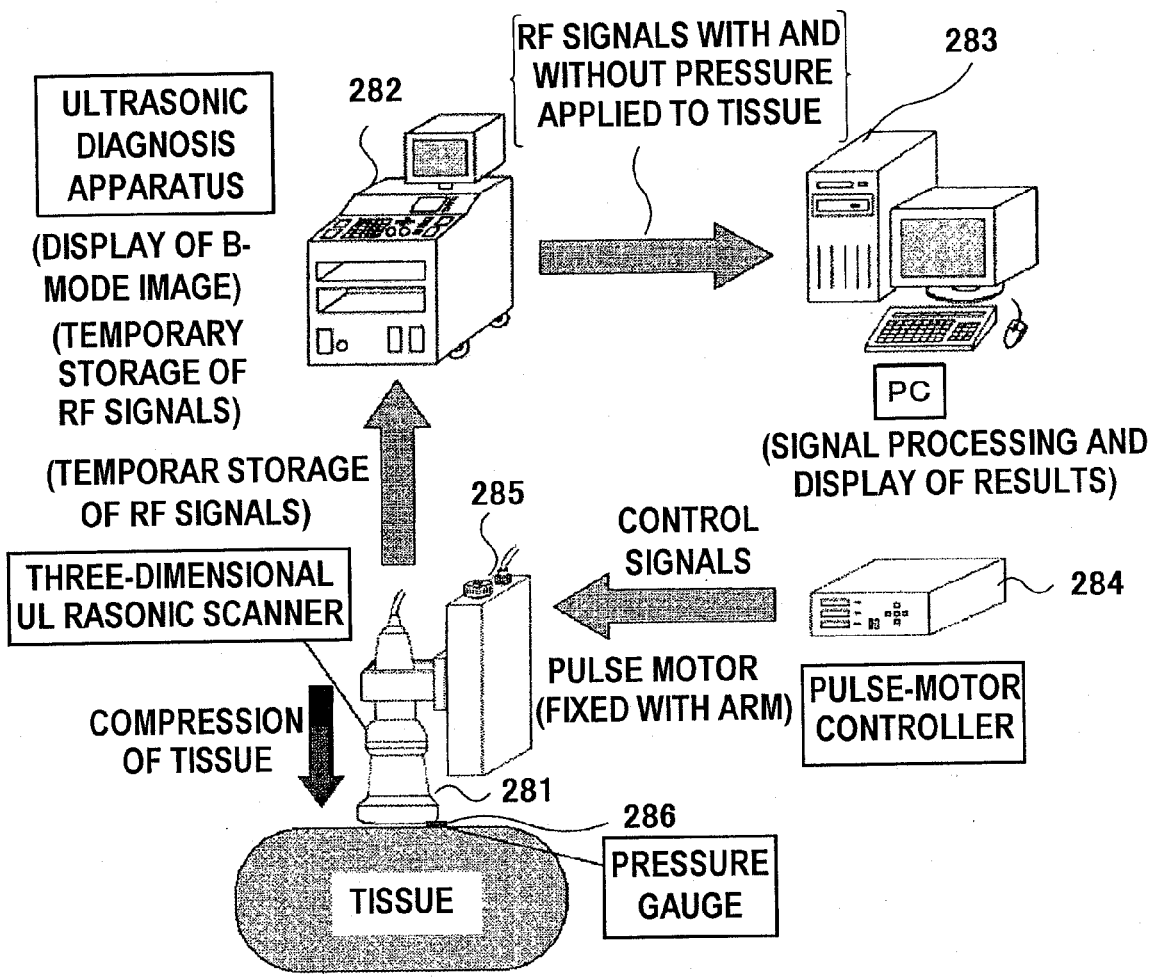
FIG. 26 is a diagram which shows a basic configuration of the ultrasonic diagnosis system.

Next, description will be made regarding a specific configuration of an ultrasonic diagnosis system employing the aforementioned expanded combined autocorrelation method and the aforementioned elastic modulus reconstructing method with the three-dimensional finite element model. FIG. 26 is a diagram which shows a basic configuration of the ultrasonic diagnosis system. The ultrasonic diagnosis system comprises a three-dimensional ultrasonic scanner 281, an ultrasonic diagnosis apparatus 282, a personal computer 283, a pulse motor controller 284, a pulse motor 285, a pressure gauge 286, and the like. The three-dimensional ultrasonic scanner 281 has functions for casting ultrasonic pulse signals toward the tissue, and for receiving ultrasonic echo signals reflected from the tissue. Note that the system employs the elastic modulus reconstructing method with the three-dimensional finite element model, and accordingly, the system requires three-dimensional data within the tissue. Accordingly, the ultrasonic diagnosis system has a configuration for making three-dimensional scanning with the three-dimensional ultrasonic scanner 281. The ultrasonic diagnosis apparatus 282 has functions for controlling the three-dimensional ultrasonic scanner 281, and for displaying real-time ultrasonic B-mode images, thereby allowing the user to determine the position of the region which is to be measured. Note that a conventional ultrasonic diagnosis apparatus may be employed as the ultrasonic diagnosis apparatus 282 without modification. The ultrasonic diagnosis apparatus includes a full-digital device having frame memory for temporarily storing the measured RF signals. The personal computer 283 receives the RF signals measured by the ultrasonic diagnosis apparatus 282, performs processing (processing proposed in the present embodiment described above) for estimating the tissue elastic properties, and displays the estimation results. The pulse motor 285 has a function for controlling the pressure applied to the tissue. The pulse motor 285 is fixed at the tip of a stationary arm, and the three-dimensional ultrasonic scanner 281 is mounted on the moving portion of the pulse motor 285. The system has a configuration wherein the pulse motor controller 284 controls the pulse motor 285 for adjusting the position of the ultrasonic scanner 281 in the vertical direction, thereby allowing the user to adjusting the pressure applied to the tissue which causes small compression thereof by several percent with high precision. The pressure gauge 286 has a function for measuring the pressure on the body surface; the pressure serving as the boundary condition required for reconstructing the elastic modulus reconstruction. Note that the pressure gauge 286 is positioned between the ultrasonic scanner 281 and the body surface. Here, the pressure measured with the pressure gauge 286 is used as the pressure on the body surface on the assumption that compression of the tissue through the ultrasonic scanner 281 causes the uniform pressure distribution on the body surface.

Figure 27:
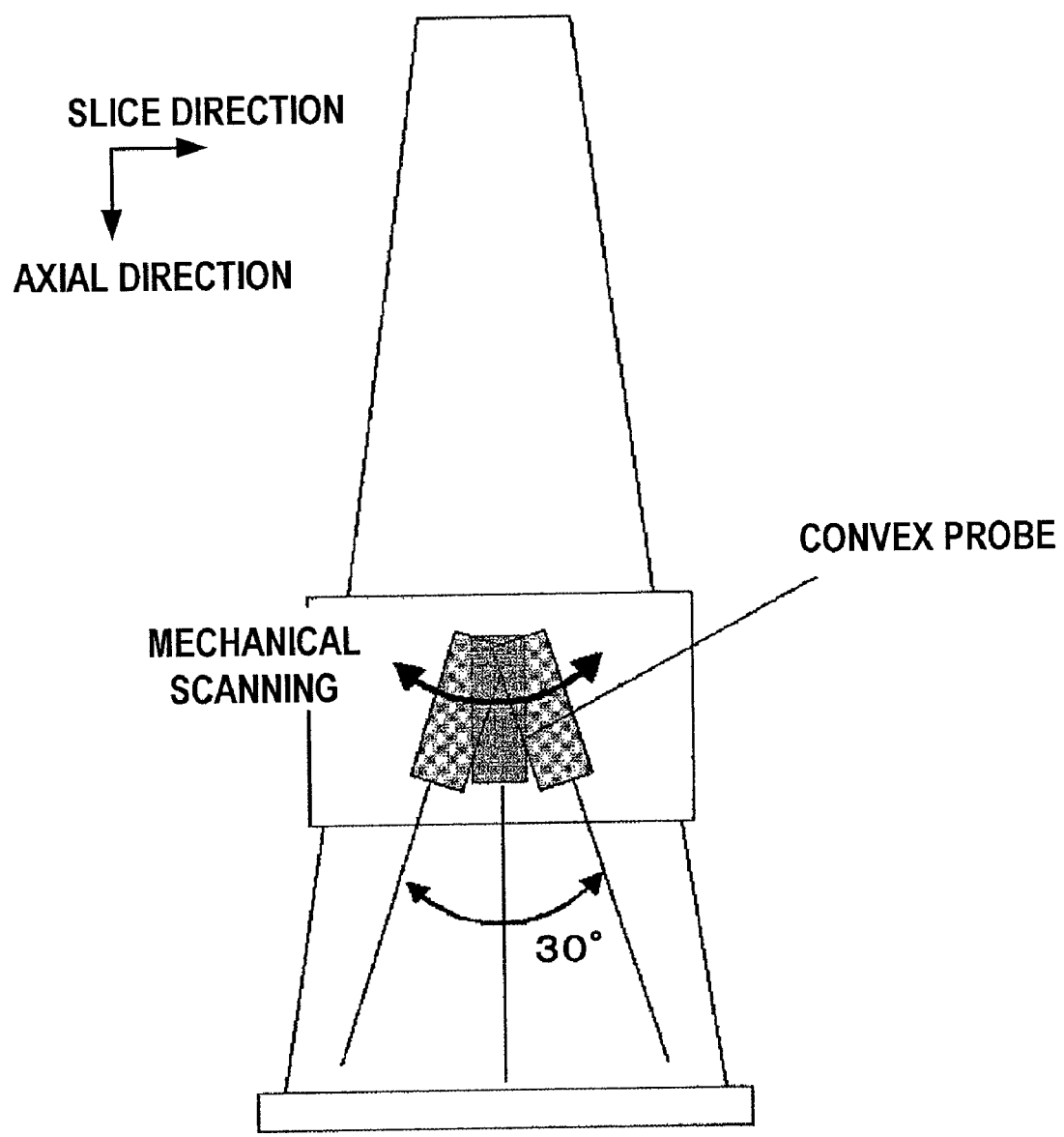
FIG. 27 is a diagram which shows a specific configuration of an ultrasonic scanner employed in the ultrasonic diagnosis system.

FIG. 27 is a diagram which shows a specific configuration of the ultrasonic scanner 281 included in the ultrasonic diagnosis system. The three-dimensional ultrasonic scanner 281 does not have a two-dimensional array configuration wherein ultrasonic transducers are two-dimensionally arrayed, but has a three-dimensional scanning configuration wherein mechanical scanning of a two-dimensional convex scanning probe is made in the slice direction in water.

The ultrasonic diagnosis system shown in FIG. 26 is designed principally for diagnosis of mammary cancer, and accordingly, the property parameters of the ultrasonic scanner are determined for diagnosis of mammary cancer. Specifically, the principal property parameters of the ultrasonic scanner used here include: the ultrasonic center frequency of 7.5 MHz, the sampling frequency of 30 MHz, the number of scanning lines of 71, the number of frames of 44, the transducer scanning angle of 30°, and the period of time for a three-dimensional scanning cycle of 0.5 seconds. Note that scanning of the convex probe is made in the slice direction by the aforementioned scanning angle of the transducer. Also, the aforementioned number of frames means the number of the scanning images (frames) acquired for a single cycle of scanning of the convex probe. On the other hand, the properties of the ultrasonic pulse obtained by actual measurement using a wire target in water include: the pulse width of approximately 0.5 mm; the beam width in the horizontal direction of approximately 1.5 mm; and the beam width in the slice direction of approximately 2.6 mm.

Next, description will be made regarding the operation of the ultrasonic diagnosis system shown in FIG. 26, which makes measurement of the elastic properties. First, the user moves the three-dimensional scanner 281 mounted on the arm so as to make positioning of the ultrasonic scanner 281 at a desired portion which is to be measured while monitoring the real-time B-mode images obtained by the ultrasonic diagnosis apparatus 282. Note that at the time of positioning of the ultrasonic scanner 281, three-dimensional scanning of the ultrasonic scanner 281 is not made (i.e., mechanical scanning of the convex probe is not made), and only the B-mode image corresponding to the center plane of the scanner is displayed on the ultrasonic diagnosis apparatus 282. The reason is that with the ultrasonic diagnosis apparatus 282 used here, the real-time B-mode images cannot be displayed at the time of three-dimensional scanning. It is needless to say that an ultrasonic diagnosis apparatus may be employed, which has a function wherein the real-time B-mode images can be displayed at the time of three-dimensional scanning, thereby allowing the user to make positioning of the three-dimensional ultrasonic scanner 281 while making three-dimensional scanning. Following positioning of the ultrasonic scanner 281 at a desired portion which is to be measured, the user fixes the moving portion of the arm in order to fix the ultrasonic scanner 281. Then, the system makes measurement of the three-dimensional RF signals without pressure applied to the tissue. Note that upon the user pressing the button for three-dimensional scanning, three-dimensional scanning is automatically made. Here, the period of time for a single cycle of the three-dimensional scanning is only 0.5 seconds. The measured RF data without application of pressure is stored in the frame memory within the ultrasonic apparatus. Subsequently, upon the user pressing the button one time for operating the pulse motor controller 284 for controlling compression of the tissue, the pulse motor 285 fixed to the arm moves the ultrasonic scanner 281 by a predetermined distance, thereby compressing the tissue through the ultrasonic scanner 281. Subsequently, the motor 285 stops while maintaining compression of the tissue. In this state, the user presses the button again for three-dimensional scanning, whereby the RF data under pressure applied to the tissue is measured. Note that the RF data under pressure applied to the tissue is stored in the frame memory included in the ultrasonic apparatus 282 in the same way as with the RF data without application of pressure. Also, the pressure applied to the tissue is measured with the pressure gauge mounted at the end of the ultrasonic scanner 281. Then, measurement ends, and the pressure applied to the tissue is released, following which the subject is freed.

Following freeing of the subject, the system accesses the frame memory included in the ultrasonic diagnosis apparatus 282 through the personal computer 283, and the RF data with and without pressure applied to the tissue is stored on a hard disk included in the personal computer 283. Such processing is performed since the frame memory included in the ultrasonic apparatus has a function for temporarily storing the data, i.e., has only a capacity for storing the data for a single measurement cycle. The personal computer 283 executes a program for calculation using the expanded combined auto-correlation method and the elastic modulus distribution reconstructing method with the three-dimensional finite element model in order to estimate the strain distribution and the elastic modulus distribution based upon the RF data with and without pressure applied to the tissue. Then, the personal computer 283 displays the B-mode image, the strain image, and the elastic modulus image, on a monitor, by executing a display program.

The ultrasonic diagnosis system using the strain distribution display method and the elastic modulus distribution display method according to the present invention has the advantage of enabling reconstruction of the elastic modulus distribution based upon the strain distribution in the ultrasonic beam direction (axial direction) alone, as well as the advantage of enabling estimation of the displacement distribution regardless of displacement in the horizontal direction.

Note that while description has been made regarding an arrangement wherein the envelope signals are employed, the present invention is not restricted to the aforementioned arrangement, rather, any parameter which represents the relation between the wave properties including the amplitude, the wave height, and the number of waves, may be employed.

The invention claimed is:

1. An ultrasonic diagnosis system comprising:
    an ultrasonic probe for performing transmission/reception of ultrasonic signals to/from a subject;
    correlation computing means for sequentially moving, at set intervals relatively in an axial direction of an ultrasonic beam, a pair of envelopes of ultrasound echo signals from the subject with and without pressure applied to the subject by the ultrasonic probe, and obtaining a maximum coefficient position where a correlation coefficient of the envelopes with and without the pressure application is greatest and a phase difference at the maximum coefficient position; and
    strain computation means for obtaining displacement of tissue of the subject due to the pressure application and strain distribution of tissue of the subject, based on the maximum coefficient position and the phase difference obtained by the correlation computing means;
    the correlation computing means including,
    a first unpressed quadrature detection circuit for performing quadrature detection of reflection echo signals without pressure application,
    a second pressed quadrature detection circuit for performing quadrature detection of reflection echo signals with the pressure application, and
    a plurality of delay circuits for sequentially delaying an output of the second pressed quadrature detection circuit each by a set amount of time,
    wherein the correlation coefficient and the phase difference are obtained based on an output of the first unpressed quadrature detection circuit and the plurality of delay circuits.

2. The ultrasonic diagnosis system according to claim 1, wherein the correlation computing means comprises:
    a first correlation computation circuit for obtaining an autocorrelation value for an envelope of a reflection echo signal without the pressure application, based on the output of the first unpressed quadrature detection circuit;
    a second correlation computation circuit for obtaining an autocorrelation value for an envelope of a reflection echo signal with the pressure application, based on the output of the second pressed quadrature detection circuit;
    a third correlation computation circuit for obtaining a cross-correlation value for the pair of reflection echo signals with and without the pressure application, based on the output of the first unpressed quadrature detection circuit and the second pressed quadrature detection circuit;
    a correlation coefficient computation circuit for obtaining the correlation coefficient for the pair of reflection echo signals with and without the pressure application, based on the correlation values obtained by each of the first correlation computation circuit, the correlation computation circuit, and the third correlation computation circuit; and
    a phase difference computation circuit for obtaining the phase difference of the pair of reflection echo signals with and without the pressure application, based on an output of the first correlation computation circuit and the correlation computation circuit.

3. The ultrasonic diagnosis system according to claim 2, further comprising:
    elastic modulus computing means for creating at least a two-dimensional finite element model by dividing the subject tissue into a finite number of elements, and computing elastic modulus distribution using the model information and a strain distribution.

4. The ultrasonic diagnosis system according to claim 2, further comprising:
    elastic modulus computing means for creating a three-dimensional finite element model by dividing the subject tissue into a finite number of rectangular parallelepiped elements under an assumption that the subject tissue exhibits isotropic elasticity and near-incompressibility, and computing an elastic modulus distribution using a strain distribution in an elastic equation under the assumption that the elastic modulus, stress, and strain are uniform within each of the elements.

5. The ultrasonic diagnosis system according to claim 1, wherein the plurality of delay circuits sequentially delay the output of the second pressed quadrature detection circuit by a time interval as great as half-wavelength of the ultrasonic signals.

6. The ultrasonic diagnosis system according to claim 5, further comprising:

elastic modulus computing means for creating at least a two-dimensional finite element model by dividing the subject tissue into a finite number of elements, and computing elastic modulus distribution using the model information and a strain distribution.

7. The ultrasonic diagnosis system according to claim 5, further comprising:
elastic modulus computing means for creating a three-dimensional finite element model by dividing the subject tissue into a finite number of rectangular parallelepiped elements under an assumption that the subject tissue exhibits isotropic elasticity and near-incompressibility, and computing an elastic modulus distribution using a strain distribution in an elastic equation under the assumption that the elastic modulus, stress, and strain are uniform within each of the elements.

8. The ultrasonic diagnosis system according to claim 1, further comprising:
elastic modulus computing means for creating at least a two-dimensional finite element model by dividing the subject tissue into a finite number of elements, and computing elastic modulus distribution using the model information and a strain distribution.

9. The ultrasonic diagnosis system according to claim 1, further comprising:
elastic modulus computing means for creating a three-dimensional finite element model by dividing the subject tissue into a finite number of rectangular parallelepiped elements under an assumption that the subject tissue exhibits isotropic elasticity and near-incompressibility, and computing an elastic modulus distribution using a strain distribution in an elastic equation under the assumption that the elastic modulus, stress, and strain are uniform within each of the elements.

10. An elastic information distribution display method comprising:
inputting ultrasonic echo signals acquired by an ultrasonic probe which comes into contact with subject tissue;
sequentially moving, at set intervals relatively in an axial direction of an ultrasonic beam, a pair of envelopes of the ultrasonic echo signals from the subject with and without pressure applied to the subject by the ultrasonic probe, and obtaining a maximum coefficient position where a correlation coefficient of the envelopes with and without the pressure application is greatest and a phase difference at the maximum coefficient position; and
obtaining a displacement of tissue of the subject due to the pressure application and a strain distribution of tissue of the subject, based on maximum coefficient position and the phase difference obtained by the step of sequentially moving; and
displaying the strain distribution;
wherein the step of sequentially moving further comprises:
performing a first quadrature detection of reflection echo signals without the pressure application,
performing a second quadrature detection of reflection echo signals with the pressure application, and
sequentially delaying the step of performing a second quadrature detection each by a set amount of time, and
wherein the correlation coefficient and the phase difference are obtained based on an output of the step of performing a first quadrature detection and the step of sequentially delaying.

11. An elastic information distribution display method according to claim 10, further comprising:
creating at least a two-dimensional finite element model by dividing the subject tissue into a finite number of elements, and computing an elastic modulus distribution using the model information and the strain distribution, wherein at least one of the strain distribution and the elastic modulus distribution are displayed in the step of displaying.

* * * * *